United States Patent
Wilson et al.

(10) Patent No.: US 11,330,975 B2
(45) Date of Patent: May 17, 2022

(54) VISUALIZATION DEVICES, SYSTEMS, AND METHODS FOR INFORMING INTRAVASCULAR PROCEDURES ON BLOOD VESSEL VALVES

(71) Applicant: InterVene, Inc., South San Francisco, CA (US)

(72) Inventors: Fletcher T. Wilson, San Francisco, CA (US); Zachary J. Malchano, Mountain View, CA (US)

(73) Assignee: InterVene, Inc., South San Francisco, CA (US)

( * ) Notice: Subject to any disclaimer, the term of this patent is extended or adjusted under 35 U.S.C. 154(b) by 480 days.

(21) Appl. No.: 16/284,883

(22) Filed: Feb. 25, 2019

(65) Prior Publication Data
US 2019/0320889 A1     Oct. 24, 2019

Related U.S. Application Data

(63) Continuation of application No. 14/498,969, filed on Sep. 26, 2014, now Pat. No. 10,231,613.
(Continued)

(51) Int. Cl.
A61B 1/313     (2006.01)
A61B 8/00      (2006.01)
(Continued)

(52) U.S. Cl.
CPC ........ *A61B 1/3137* (2013.01); *A61B 1/00082* (2013.01); *A61B 1/018* (2013.01);
(Continued)

(58) Field of Classification Search
CPC . A61B 1/3137; A61B 5/0084; A61B 5/02007; A61B 8/0858; A61B 8/0891;
(Continued)

(56) References Cited

U.S. PATENT DOCUMENTS 3,704,711 A     12/1972 Park
4,898,574 A      2/1990 Uchiyama et al.
(Continued)

FOREIGN PATENT DOCUMENTS

CA     1281381 C      3/1991
CA     2678971 A1     8/2008
(Continued)

OTHER PUBLICATIONS

Corcos, I., "A new autologous venous valve by intimal flap: One cases report." Note Di Tecnica, Minerva Cardioangiol, 2003, 51, 10 pages.
(Continued)

*Primary Examiner* — Jonathan Cwern
(74) *Attorney, Agent, or Firm* — Perkins Coie LLP

(57) ABSTRACT

The present technology relates generally to devices and methods for intravascular evaluation of blood vessels. Many embodiments of the technology relate to the intravascular evaluation of blood vessels before, during and after creation of autologous valves. In one embodiment, for example, the present technology is directed to a method comprising intravascularly delivering a delivery catheter to a target location adjacent a vessel wall and engaging the vessel wall along a portion of the delivery catheter. The method can further include determining the location of a first circumferential periphery of a dissection pouch formed within the vessel wall, determining the location of a second circumferential periphery of the dissection pouch, and determining an angular width of the dissection pouch based on the location of the first circumferential periphery and the second circumferential periphery.

13 Claims, 27 Drawing Sheets

Related U.S. Application Data

(60) Provisional application No. 61/883,971, filed on Sep. 27, 2013.

(51) Int. Cl.
| | |
|---|---|
| *A61B 5/00* | (2006.01) |
| *A61B 17/04* | (2006.01) |
| *A61B 17/12* | (2006.01) |
| *A61M 25/10* | (2013.01) |
| *A61B 8/08* | (2006.01) |
| *A61B 5/02* | (2006.01) |
| *A61B 1/00* | (2006.01) |
| *A61B 1/018* | (2006.01) |
| *A61B 8/12* | (2006.01) |
| *A61B 17/00* | (2006.01) |
| *A61B 17/06* | (2006.01) |
| *A61B 17/3203* | (2006.01) |
| *A61B 17/22* | (2006.01) |
| *A61B 17/32* | (2006.01) |
| *A61B 90/00* | (2016.01) |

(52) U.S. Cl.
CPC .............. *A61B 5/00* (2013.01); *A61B 5/0066* (2013.01); *A61B 5/0084* (2013.01); *A61B 5/02007* (2013.01); *A61B 8/00* (2013.01); *A61B 8/0858* (2013.01); *A61B 8/0891* (2013.01); *A61B 8/12* (2013.01); *A61B 17/0482* (2013.01); *A61B 17/12136* (2013.01); *A61M 25/10* (2013.01); *A61M 25/1002* (2013.01); *A61B 17/3203* (2013.01); *A61B 90/39* (2016.02); *A61B 2017/00115* (2013.01); *A61B 2017/00199* (2013.01); *A61B 2017/00783* (2013.01); *A61B 2017/0409* (2013.01); *A61B 2017/0417* (2013.01); *A61B 2017/06052* (2013.01); *A61B 2017/22071* (2013.01); *A61B 2017/320044* (2013.01)

(58) Field of Classification Search
CPC ......... A61B 8/00; A61B 5/00; A61B 17/0482; A61B 17/12136; A61B 1/00082; A61B 1/018; A61B 5/0066; A61B 8/12; A61B 90/39; A61B 17/3203; A61B 2017/22071; A61B 2017/320044; A61B 2017/00115; A61B 2017/00199; A61B 2017/00783; A61B 2017/0409; A61B 2017/0417; A61B 2017/06052; A61M 25/1002; A61M 25/10

See application file for complete search history.

(56) References Cited

U.S. PATENT DOCUMENTS

| | | | |
|---|---|---|---|
| 4,932,962 A | 6/1990 | Yoon et al. | |
| 5,112,339 A | 5/1992 | Zelman et al. | |
| 5,190,046 A | 3/1993 | Shturman et al. | |
| 5,372,601 A | 12/1994 | Lary et al. | |
| 5,443,443 A | 8/1995 | Shiber et al. | |
| 5,464,395 A | 11/1995 | Faxon et al. | |
| 5,601,588 A | 2/1997 | Tonomura et al. | |
| 5,606,975 A * | 3/1997 | Liang ...................... | A61B 8/12 600/437 |
| 5,695,507 A | 12/1997 | Auth | |
| 5,738,901 A | 4/1998 | Wang et al. | |
| 5,795,322 A | 8/1998 | Boudewijn | |
| 5,810,847 A | 9/1998 | Laufer et al. | |
| 5,836,945 A | 11/1998 | Perkins | |
| 5,989,276 A | 11/1999 | Houser et al. | |
| 6,190,353 B1 | 2/2001 | Makower et al. | |
| 6,375,635 B1 | 4/2002 | Moutafis et al. | |
| 6,379,319 B1 | 4/2002 | Garibotto et al. | |
| 6,344,027 B1 | 5/2002 | Goll | |
| 6,475,226 B1 * | 11/2002 | Belef ................... | A61B 1/3137 606/170 |
| 6,506,178 B1 | 1/2003 | Schubart et al. | |
| 6,514,217 B1 | 2/2003 | Selmon et al. | |
| 6,524,251 B2 | 2/2003 | Rabiner et al. | |
| 6,676,665 B2 | 1/2004 | Foley et al. | |
| 6,685,648 B2 | 2/2004 | MacAulay et al. | |
| 6,692,466 B1 | 2/2004 | Chow et al. | |
| 6,702,744 B2 | 3/2004 | Mandrusov et al. | |
| 6,758,836 B2 | 7/2004 | Zawacki et al. | |
| 6,902,576 B2 | 6/2005 | Drasler et al. | |
| 7,008,411 B1 | 3/2006 | Mandrusov et al. | |
| 7,056,325 B1 | 6/2006 | Makower et al. | |
| 7,150,738 B2 | 12/2006 | Ray et al. | |
| 7,179,249 B2 | 2/2007 | Steward et al. | |
| 7,273,469 B1 | 9/2007 | Chan et al. | |
| 7,357,795 B2 | 4/2008 | Kaji et al. | |
| 7,517,352 B2 | 4/2009 | Evans et al. | |
| 7,775,968 B2 | 8/2010 | Mathis | |
| 7,780,592 B2 | 8/2010 | Tronnes et al. | |
| 7,918,870 B2 | 4/2011 | Kugler et al. | |
| 7,927,305 B2 | 4/2011 | Yribarren et al. | |
| 7,938,819 B2 | 5/2011 | Atkinson et al. | |
| 7,955,346 B2 | 6/2011 | Mauch et al. | |
| 8,025,655 B2 | 9/2011 | Atkinson et al. | |
| 8,083,727 B2 | 12/2011 | Kugler et al. | |
| 8,100,860 B2 | 1/2012 | Von Oepen et al. | |
| 8,114,123 B2 | 2/2012 | Brenzel et al. | |
| 8,267,947 B2 | 9/2012 | Ellingwood et al. | |
| 8,323,261 B2 | 12/2012 | Atkinson et al. | |
| 8,460,316 B2 | 6/2013 | Wilson et al. | |
| 8,636,712 B2 | 1/2014 | Atkinson et al. | |
| 8,753,366 B2 | 6/2014 | Makower et al. | |
| 9,320,504 B2 | 4/2016 | Wilson et al. | |
| 9,381,034 B2 | 7/2016 | Kawwei | |
| 9,545,289 B2 | 1/2017 | Yu et al. | |
| 10,874,413 B2 | 12/2020 | Wilson et al. | |
| 2001/0041899 A1 | 11/2001 | Foster | |
| 2002/0029052 A1 | 3/2002 | Evans et al. | |
| 2002/0072706 A1 | 6/2002 | Hiblar et al. | |
| 2002/0091362 A1 | 7/2002 | Maginot et al. | |
| 2002/0103459 A1 | 8/2002 | Sparks et al. | |
| 2004/0167558 A1 | 8/2004 | Igo et al. | |
| 2004/0215339 A1 | 10/2004 | Drasler et al. | |
| 2005/0014995 A1 | 1/2005 | Amundson et al. | |
| 2005/0075665 A1 | 4/2005 | Brenzel et al. | |
| 2005/0165466 A1 | 7/2005 | Morris et al. | |
| 2005/0273159 A1 | 12/2005 | Opie et al. | |
| 2006/0094929 A1 | 5/2006 | Tronnes et al. | |
| 2006/0136045 A1 | 6/2006 | Flagle et al. | |
| 2006/0156875 A1 | 7/2006 | McRury et al. | |
| 2006/0178646 A1 | 8/2006 | Harris et al. | |
| 2006/0184187 A1 | 8/2006 | Surti | |
| 2006/0235449 A1 | 10/2006 | Schubart et al. | |
| 2006/0271090 A1 | 11/2006 | Shaked et al. | |
| 2007/0005093 A1 | 1/2007 | Cox et al. | |
| 2007/0093780 A1 | 4/2007 | Kugler et al. | |
| 2007/0093781 A1 | 4/2007 | Kugler et al. | |
| 2007/0208368 A1 | 9/2007 | Katoh et al. | |
| 2008/0033467 A1 | 2/2008 | Miyamoto et al. | |
| 2008/0103480 A1 * | 5/2008 | Bosel .................. | A61M 25/0021 604/513 |
| 2008/0228171 A1 | 9/2008 | Kugler et al. | |
| 2008/0228211 A1 | 9/2008 | Gonon | |
| 2008/0243065 A1 | 10/2008 | Rottenberg et al. | |
| 2009/0005793 A1 | 1/2009 | Pantages et al. | |
| 2009/0112059 A1 | 4/2009 | Nobis et al. | |
| 2009/0149739 A9 | 6/2009 | Maschke | |
| 2009/0182192 A1 | 7/2009 | Shiono et al. | |
| 2009/0209910 A1 | 8/2009 | Kugler et al. | |
| 2009/0254051 A1 | 10/2009 | Von Oepen et al. | |
| 2009/0270799 A1 | 10/2009 | Seto et al. | |
| 2010/0076476 A1 | 3/2010 | To et al. | |
| 2010/0152682 A1 | 6/2010 | Mauch et al. | |
| 2010/0152843 A1 | 6/2010 | Mauch et al. | |
| 2010/0241147 A1 | 9/2010 | Maschke | |
| 2010/0256599 A1 | 10/2010 | Kassab et al. | |

(56) References Cited

U.S. PATENT DOCUMENTS

| | | |
|---|---|---|
| 2011/0264125 A1* | 10/2011 | Wilson .......... A61B 17/320016 606/159 |
| 2011/0264127 A1 | 10/2011 | Mauch et al. |
| 2011/0264128 A1 | 10/2011 | Mauch et al. |
| 2012/0143234 A1 | 6/2012 | Wilson et al. |
| 2012/0289987 A1 | 11/2012 | Wilson et al. |
| 2013/0066346 A1 | 3/2013 | Pigott et al. |
| 2013/0103070 A1 | 4/2013 | Kugler et al. |
| 2013/0116715 A1 | 5/2013 | Weber |
| 2013/0216114 A1 | 8/2013 | Courtney et al. |
| 2013/0317534 A1 | 11/2013 | Zhou et al. |
| 2014/0012301 A1 | 1/2014 | Wilson et al. |
| 2015/0057566 A1 | 2/2015 | Vetter et al. |
| 2015/0094532 A1 | 4/2015 | Wilson et al. |
| 2015/0265263 A1 | 9/2015 | Wilson et al. |
| 2015/0342631 A1 | 12/2015 | Wilson et al. |
| 2015/0359630 A1 | 12/2015 | Wilson et al. |
| 2016/0166243 A1 | 6/2016 | Wilson et al. |
| 2016/0235428 A1 | 8/2016 | Wilson et al. |
| 2017/0035450 A1 | 2/2017 | Fletcher et al. |
| 2017/0035455 A1 | 2/2017 | Fletcher et al. |
| 2018/0000509 A1 | 1/2018 | Wilson et al. |
| 2018/0214173 A1 | 8/2018 | Wilson et al. |
| 2018/0289441 A1 | 10/2018 | Wilson et al. |
| 2018/0333166 A1 | 11/2018 | Wilson et al. |

FOREIGN PATENT DOCUMENTS

| | | |
|---|---|---|
| CN | 1907243 A | 2/2007 |
| CN | 1957861 A | 5/2007 |
| JP | 2002514111 A | 5/2002 |
| JP | 2003033357 A | 2/2003 |
| JP | 2003267160 A | 9/2003 |
| JP | 2009165822 A | 7/2009 |
| JP | 2009183516 A | 8/2009 |
| RU | 2108751 C1 | 4/1998 |
| RU | 2160057 C2 | 12/2000 |
| WO | 99000059 A1 | 1/1999 |
| WO | 2008/063621 A2 | 5/2008 |
| WO | 2010074853 A1 | 7/2010 |
| WO | 2011106735 A1 | 9/2011 |
| WO | 2012145444 A2 | 10/2012 |
| WO | 2013119849 A1 | 8/2013 |
| WO | 2014110460 A1 | 7/2014 |

OTHER PUBLICATIONS

Lugli, M., et al., Neovalve construction in the deep venous incompetence. J. Vasc. Surg., Jan. 2009, 49(1), 156-62.

Maleti, O., Neovalve construction in postthrombotic syndrome. Journal of Vascular Surgery, vol. 34, No. 4, 6 pages.

* cited by examiner

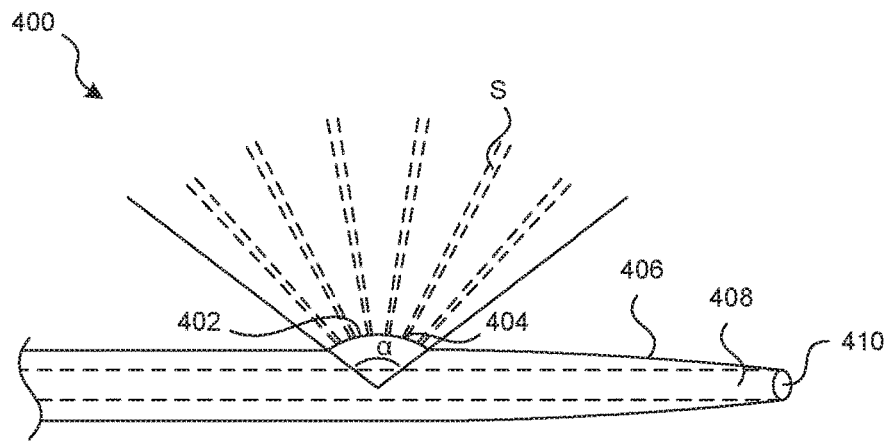 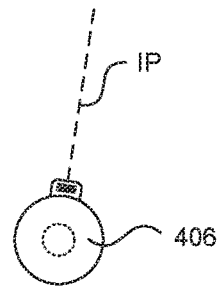
FIG. 4A      FIG. 4B
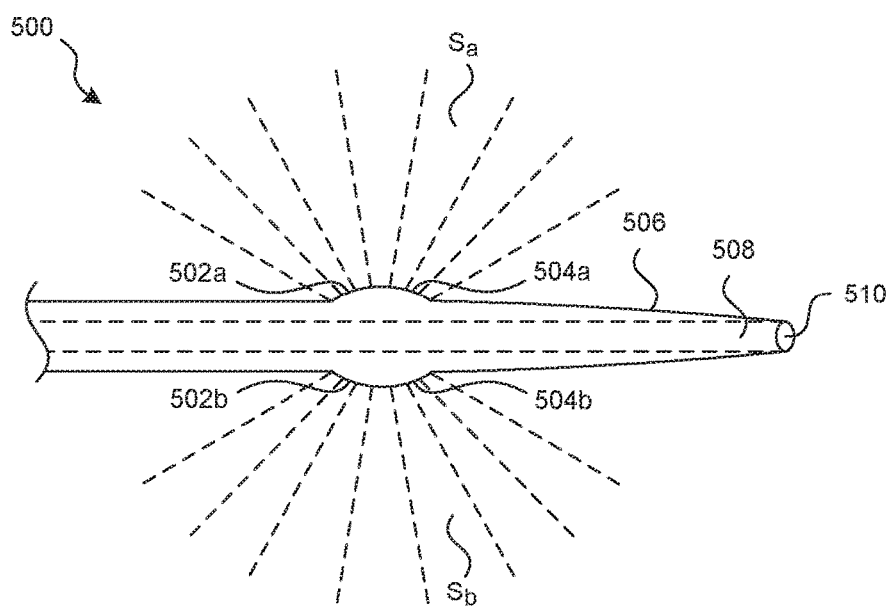 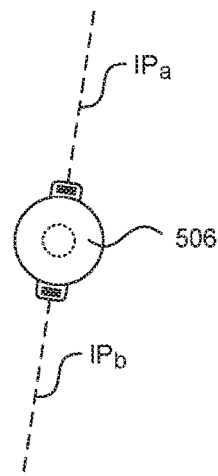
FIG. 5A      FIG. 5B

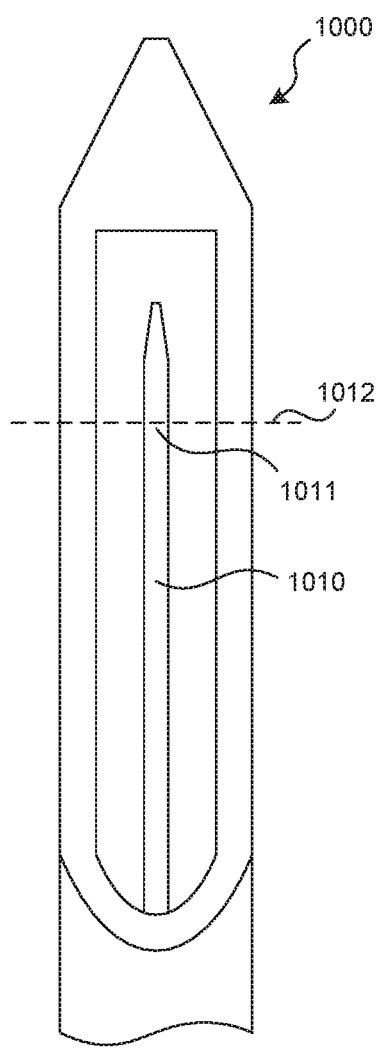 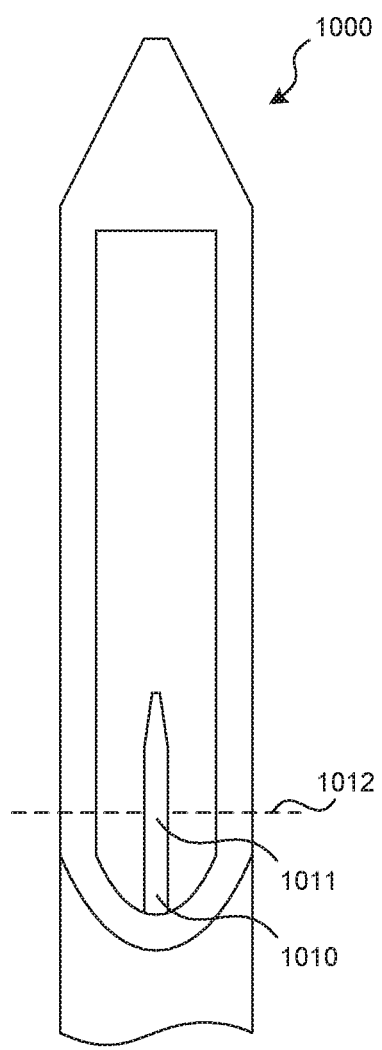
*FIG. 10B*  *FIG. 10C*

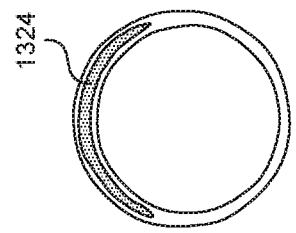
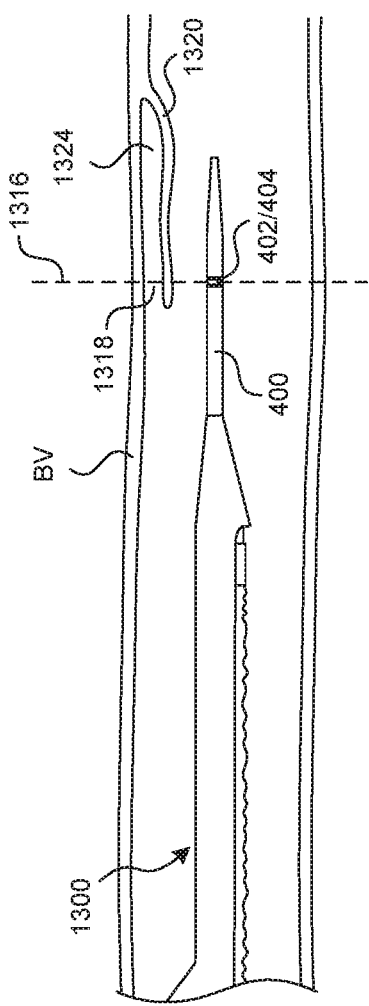
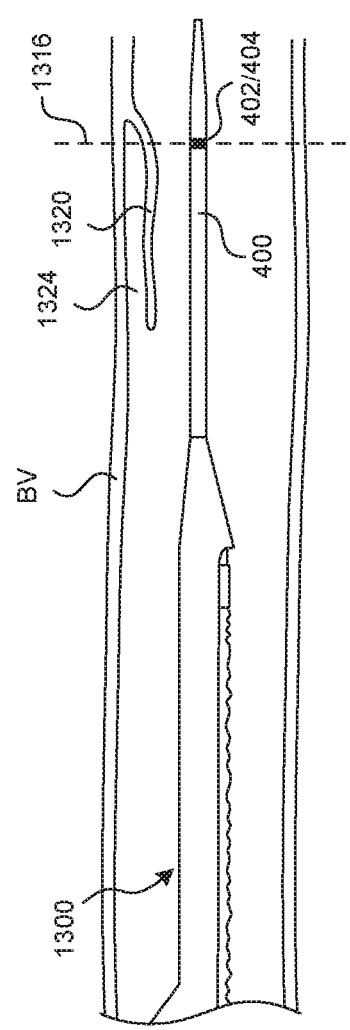
FIG. 13A
FIG. 13B
FIG. 13C
FIG. 13D

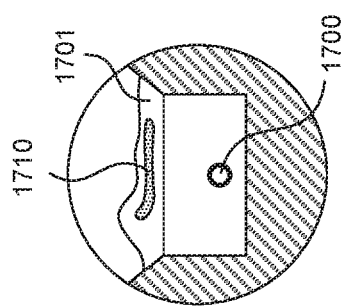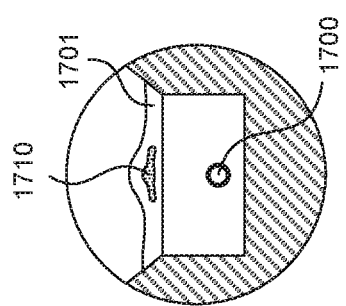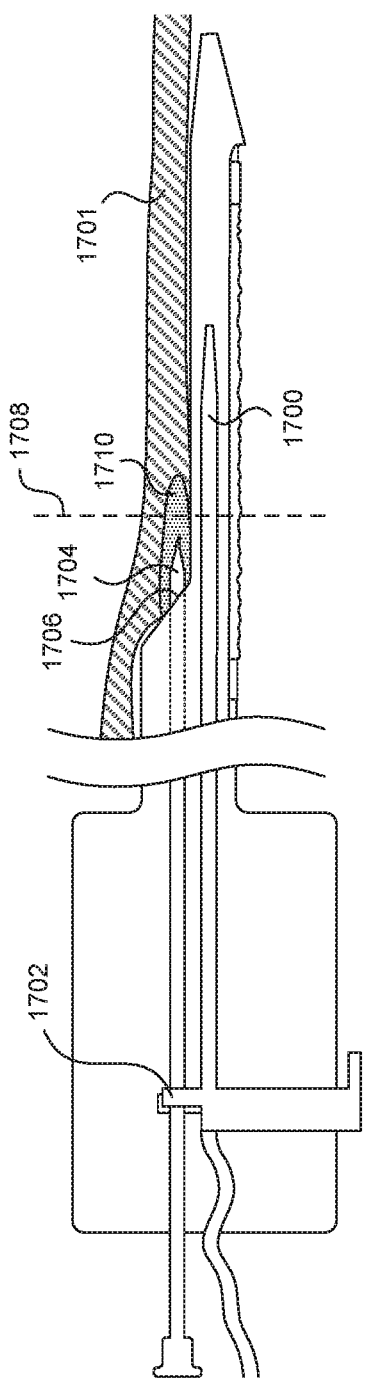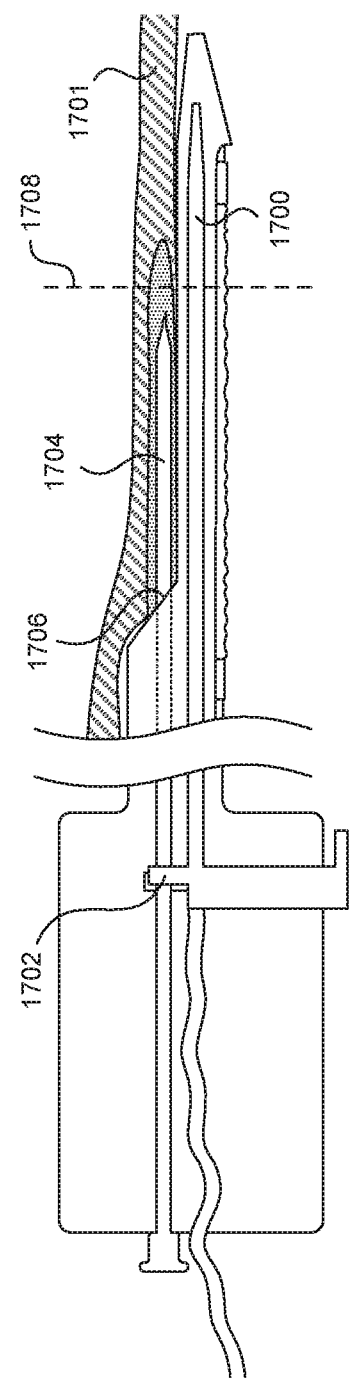

VISUALIZATION DEVICES, SYSTEMS, AND METHODS FOR INFORMING INTRAVASCULAR PROCEDURES ON BLOOD VESSEL VALVES

CROSS-REFERENCE TO RELATED APPLICATIONS

The present application is a continuation of U.S. patent application Ser. No. 14/498,969, filed Sep. 26, 2014, now U.S. Pat. No. 10,231,613, which claims the benefit of U.S. Provisional Patent Application No. 61/883,971, filed Sep. 27, 2013, which are incorporated herein by reference in their entirety.

TECHNICAL FIELD

The present technology relates generally to devices and methods for intravascular evaluation of blood vessels. Many embodiments of the technology relate to the intravascular evaluation of blood vessels before, during and after creation of autologous valves.

BACKGROUND

Venous reflux is a medical condition affecting the circulation of blood that is caused by one or more faulty valves in a blood vessel. As a result, blood is allowed to flow upstream, causing unwanted clinical problems. Accordingly, there is a need for devices and methods that address one or more of these deficiencies.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 4A is a side view of a visualization device configured in accordance with an embodiment of the present technology.

FIG. 4B is a cross-sectional end view of the visualization device shown in FIG. 4A taken along line 4B-4B.

FIG. 5A is a side view of a visualization device configured in accordance with another embodiment of the present technology.

FIG. 5B is a cross-sectional end view of the visualization device shown in FIG. 5A taken along line 5B-5B.

FIGS. 10B and 10C are top plan views, of a delivery catheter and a visualization device used to provide a three-dimensional image of a blood vessel or other tissue in accordance with the present technology.

FIG. 13A is a side view of the operation of a visualization device in accordance with the present technology.

FIG. 13B depicts an image provided by the visualization device of FIG. 13A.

FIG. 13C is a side view of the operation of the visualization device shown in FIG. 13A at a another location in accordance with the present technology.

FIG. 13D depicts an image provided by the visualization device at the location shown in FIG. 13C.

FIG. 17A is a side view of a system having a link actuation mechanism that moves a tool (e.g., a puncture tool) and a visualization device in accordance with the present technology.

FIG. 17B depicts an image provided by the system of FIG. 17A.

FIG. 17C is a side view of the system of FIG. 17A with the tool and the visualization device at a different location.

FIG. 17D depicts an image provided by the system of FIG. 17C.

DETAILED DESCRIPTION

The devices, systems and methods of the present technology provide in-procedure evaluation of vessel wall states specific to vessel wall apposition and dissection. Specific details of several embodiments of treatment devices, systems and associated methods in accordance with the present technology are described below with reference to FIGS. 1A-21B. Although many of the embodiments are described below with respect to devices, systems, and methods for intravascular creation of autologous venous valves, other applications and other embodiments in addition to those described herein are within the scope of the technology. For example, the devices, systems and methods of the present technology can be used in any bodily cavity (including arterial and venous blood vessels) and used for surgical creation of autologous valves, or repair of autologous or synthetic valves. Additionally, several other embodiments of the technology can have different states, components, or procedures than those described herein. Moreover, it will be appreciated that specific elements, substructures, advantages, uses, and/or other features of the embodiments described with reference to FIGS. 1A-21B can be suitably interchanged, substituted or otherwise configured with one another in accordance with additional embodiments of the present technology. Furthermore, suitable elements of the embodiments described with reference to FIGS. 1A-21B can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1A-21B.

With regard to the terms "distal" and "proximal" within this description, unless otherwise specified, the terms can reference a relative position of the portions of a delivery catheter and/or an associated delivery device with reference to an operator and/or a location in the vasculature.

I. Selected Embodiments of Treatment Devices

Figure 1A:
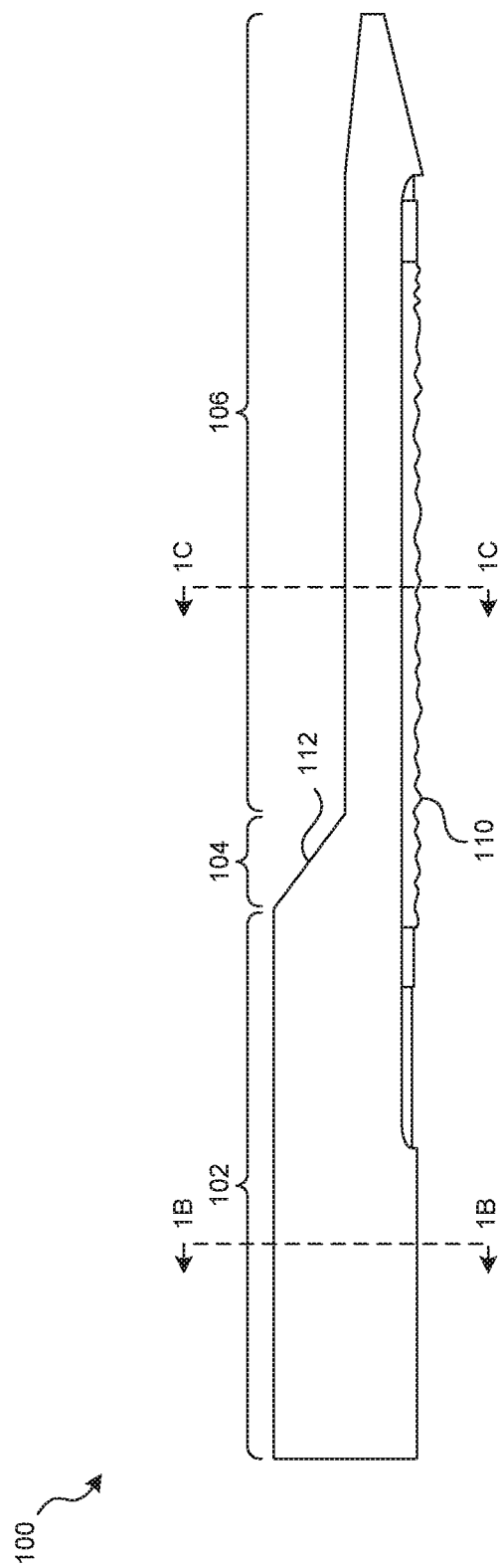
FIG. 1A is a side view configured in accordance with the present technology.

FIG. 1A is a side view of a distal portion 100 of a delivery catheter configured in accordance with the present technology. A proximal portion (not shown) of the delivery catheter is configured to be positioned external to the patient while the distal portion 100 of the delivery catheter is positioned intravascularly at a treatment site. As shown in FIG. 1A, the distal portion 100 can include a first portion 102, an intermediate portion 104, and a second portion 106. The first portion 102 can have a greater cross-sectional area than the second portion 106, and the intermediate portion 104 can have a surface that is angled or slanted inwardly in the direction of the second portion 106. The first portion 102, intermediate portion 104, and/or second portion 106 can be made from one or more plastics and/or metals, such as polyether ether ketone ("PEEK"), polycarbonate, stainless steel, and/or other generally rigid materials.

Figure 1B:
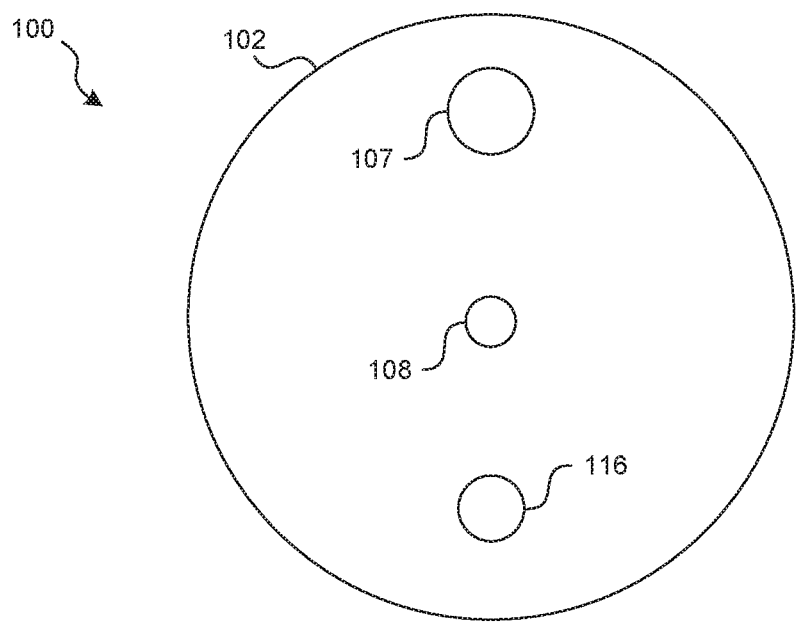
FIG. 1B is a cross-sectional end view of the delivery catheter shown in FIG. 1A taken along line 1B-1B.
Figure 1C:
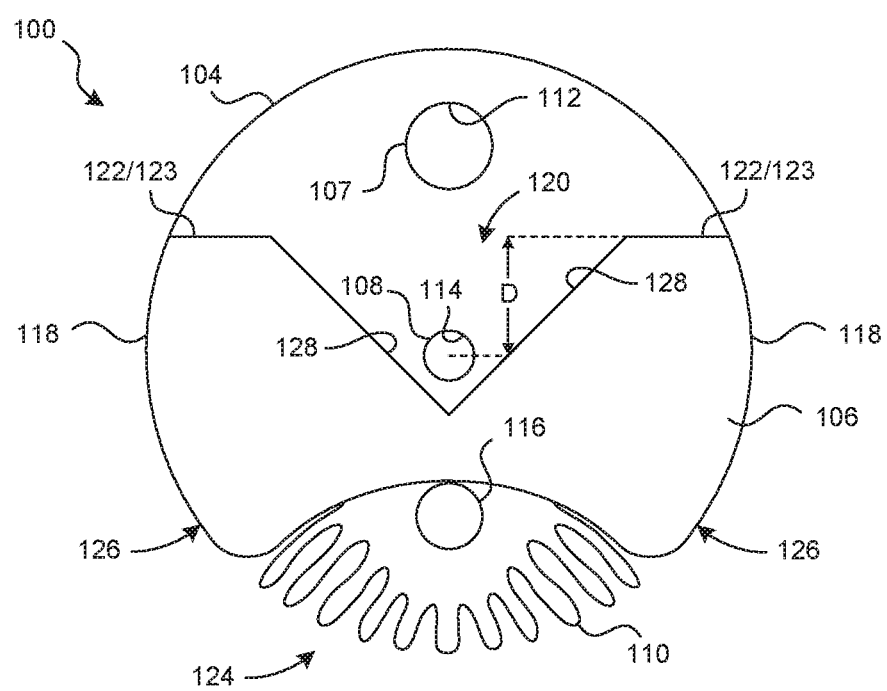
FIG. 1C is a cross-sectional end view of the delivery catheter shown in FIG. 1A taken along line 1C-1C.

FIGS. 1B and 1C are cross-sectional views of the first and second portions 102, 106, respectively. Referring to FIGS. 1B and 1C together, the delivery catheter 100 can include a device lumen 107, a visualization lumen 108, an expansion lumen 116, and an expandable element 110 (FIG. 1C) that is fluidically coupled to the expansion lumen 116. The device lumen 107 can be configured to slidably receive one or more interventional devices and extend distally from the proximal portion of the delivery catheter to an exit port 112 (FIG. 1C) positioned along the slanted surface of the intermediate portion 104.

The visualization lumen 108 can be configured to slidably receive one or more visualization devices, such as an intravascular ultrasound ("IVUS") device, an optical coherence tomography ("OCT") device, and/or other suitable visualization devices. The visualization lumen 108 can extend distally from the proximal portion of the delivery catheter to an exit port 114 (FIG. 1C) positioned proximal to the second portion 106. For example, in some embodiments the exit port 114 of the visualization lumen 108 can be positioned at the juncture between the intermediate portion 104 and the second portion 106. Additionally, in some embodiments the second portion 106 can include an elongated, tubular visualization lumen shaft (not shown) that extends distally from the exit port 114 through a trough of the second portion 106.

The expansion lumen 116 can extend distally from the proximal portion of the delivery catheter to one or more transition elements (not shown) that are configured to fluidically couple the expansion lumen 116 to the expandable element 110. For example, in embodiments where the expandable element 110 is a balloon or similar inflatable structure, the expansion lumen 116 can be fluidically coupled to the balloon via one or more inflation ports (not shown). Additionally, the expandable element 110 can be positioned on the second portion 106 at a location that is circumferentially opposite a tissue engaging portion of the second portion 106, as described in greater detail below.

Referring now to FIGS. 1A and 1C, the second portion 106 can define a trough that extends distally in a longitudinal direction from the first portion 102 and/or intermediate portion 104. For example, the distal portion 106 can have a bottom portion 124, one or more sidewalls 118 that extend from the bottom portion 124, and one or more tissue engaging portions 122 along the sidewalls 118. As shown in FIG. 1C, each of the sidewalls 118 can include a curved exterior surface 126, a generally flat superior surface 123 that defines at least part of the tissue engaging portions 122, and a linear interior surface 128 that defines the trough. The interior surfaces 128 of the second portion 106 can form a v-shaped cavity 120 (e.g., trough) that extends distally from the intermediate portion 104 to the distal-most point of the delivery catheter. Such a configuration can be advantageous as the v-shaped intersection 130 of the interior portions 128 can slidably receive and guide a visualization device (not shown) through the trough. In other embodiments, the exterior surfaces 126, superior surfaces 123, and interior surfaces 128 can have other shapes and/or configurations. For example, in some embodiments the exterior surfaces 126 can be linear and/or rounded surfaces, the superior surfaces can be non-flat (e.g., angled, rounded, including or more protrusions, including one or more recesses, etc.), and/or the interior surfaces 128 can be linear and/or a combination of linear and rounded surfaces. Likewise, although the cavity shown in FIG. 1C is v-shaped, in other embodiments the cavity 120 can have other suitable configurations, such as square (see FIG. 3), rounded, etc.

In the embodiment shown in FIGS. 1A-1C, the tissue engaging portions 122 correspond to the superior surfaces (referred to collectively as 123 and individually as first and second superior surfaces 123a-b). In other embodiments, however, the tissue engaging portions 122 can additionally or alternatively correspond to one or more non-superior surfaces of the sidewalls 118 (e.g., a side or radially exterior portion of the sidewalls). Additionally, in some embodiments the superior surfaces of the sidewalls can have one or more protrusions (not shown) or other features that extend superiorly from the superior surface to engage the targeted tissue. In general, the tissue engaging portions 122 define a reference surface or reference portion that positions a portion of a vessel wall at a known location with respect to the device lumen 107 and the visualization lumen 108.

Referring to FIG. 1C, the relative positions of the device lumen exit port 112, visualization lumen exit port 114, and sidewalls 118 of the present technology improve tissue engagement and visualization. For example, the center of the device lumen exit port 112 can be positioned midway between the interior surfaces of the sidewalls 118, and at least a portion of the device lumen exit port 112 can be at an elevation corresponding to an elevation of the tissue engaging portion 122. In one embodiment, the center of the device lumen exit port 112 can be positioned midway between the interior surfaces of the sidewalls 118 at an elevation corresponding at least substantially to the elevation of the tissue engaging portion 122 (see, e.g., FIG. 18). Additionally, the center of the visualization lumen exit port 114 can be at an elevation that is that is a distance D from an elevation of the tissue engaging portions 122. As a result, the present technology forces the vessel wall to remain a fixed distance from a visualization device, which can be used to inform signal output and processing. In some embodiments, the distance D may be between about 0.01 mm and about 3 mm. In particular embodiments, the distance D can be between about 0.015 mm and about 1 mm. Additionally, the distance D can be between about 0.025 mm and about 0.50 mm. The arrangement shown in FIG. 1C accordingly positions the tissue at a precise, known distance from the device lumen exit port 112 and the visualization lumen exit port 114 for good visualization and dissection.

Another advantage that the high definition visual configuration shown in FIG. 1C can provide is the use of elastography to detect small differences in physical parameters within a tissue structure such as fibrotic cells, internal stresses or strains, leaflets verses endothelium, and any other subtle differences in tissue structure that may be advantages for a physician. There are many ways to perform elastography in this configuration. For example, the expandable element 110 can be inflated or deflated during imaging to dynamically change the strain within the wall during imaging to perform strain-based elastography. Additionally, an acoustic radiation force impulse imaging modality, which emits pusher beams to locally deform the tissue, can be used in addition to emitting imaging or tracking beams. These beams can be optimized for exerting ideal deformation forces in this configuration due to the controlled distance between the tissue and the transmitters. Certain tissues within the vein wall may only exhibit very subtle differences in elasticity, and therefore high definition imaging will be required to differentiate these. For example, differentiating fibrotic tissue and integrated clot, may require very high definition elastography.

Figure 2:
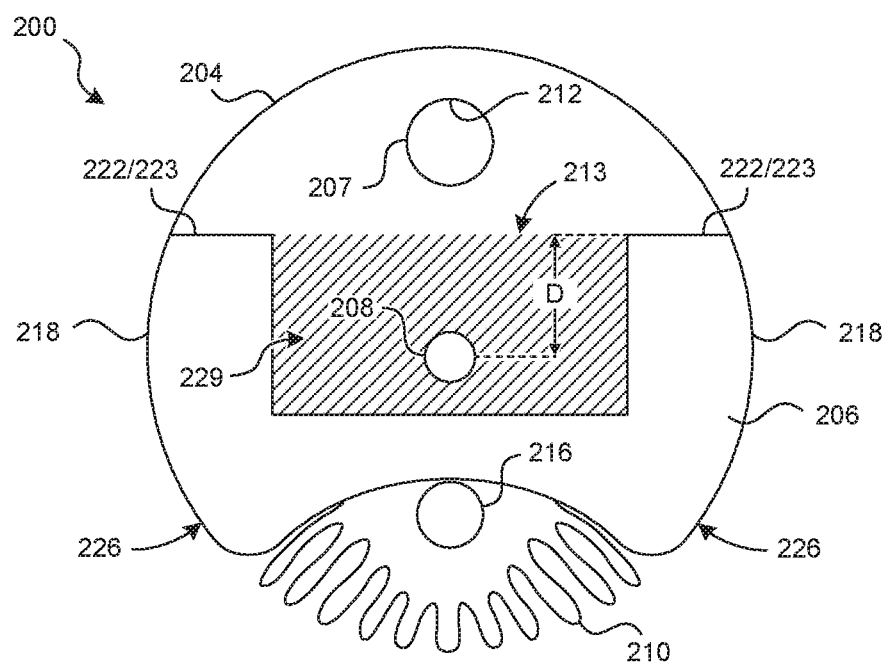
FIG. 2 is a cross-sectional end view of a second portion of a delivery catheter configured in accordance with the present technology.

FIG. 2 is a cross-sectional end view of another embodiment of a second portion 206 of a catheter 200 configured in accordance with the present technology. The catheter 200 is similar to the catheter 100 and can have a first portion 204, a second portion 206, a device lumen 207, a visualization lumen 208, an inflation lumen 216, and an expandable element 210 fluidically coupled to the inflation lumen 216. Additionally, the catheter 200 can include sidewalls 218, tissue engaging portions 222 that define a superior surface 213, and an interior surface 228 that the fines a cavity 229. The second portion 206 of the catheter can include an optional echolucent material 211 between the sidewalls 218, and the visualization lumen 208 extends distally from the intermediate portion (not shown) through the echolucent material 211 to the distal-most point of the catheter 100. As used herein, "echolucent" refers to any material configured to achieve reduced levels of sonic scattering, sonic absorption, sonic reflection, and sonic refraction. Such materials can include room-temperature vulcanizing ("RTV") silicone, soft adhesives, hard adhesives, epoxy, urethane, plastics and/or other suitable materials. As such, when a visualization device (not shown) is advanced through the second portion 206, visualization can be achieved through the echolucent material 211 to gain information regarding anatomical conditions adjacent a superior surface 213 of the echolucent material 211. Although in FIG. 2 the echolucent material 211 is shown having a rectangular shape, in other embodiments the echolucent material 211 can have any shape (e.g., rounded, square, triangular, pentagonal, etc.). Moreover, in some embodiments the visualization lumen 208 can be a separate tube extending through the echolucent material 211, and in some embodiments the echolucent material 211 can be formed to include an elongated, tubular cavity that can serve as the visualization lumen. It will be appreciated that the catheter 200 may not include the echolucent material 211 such that the cavity 229 remains open.

Figure 3:
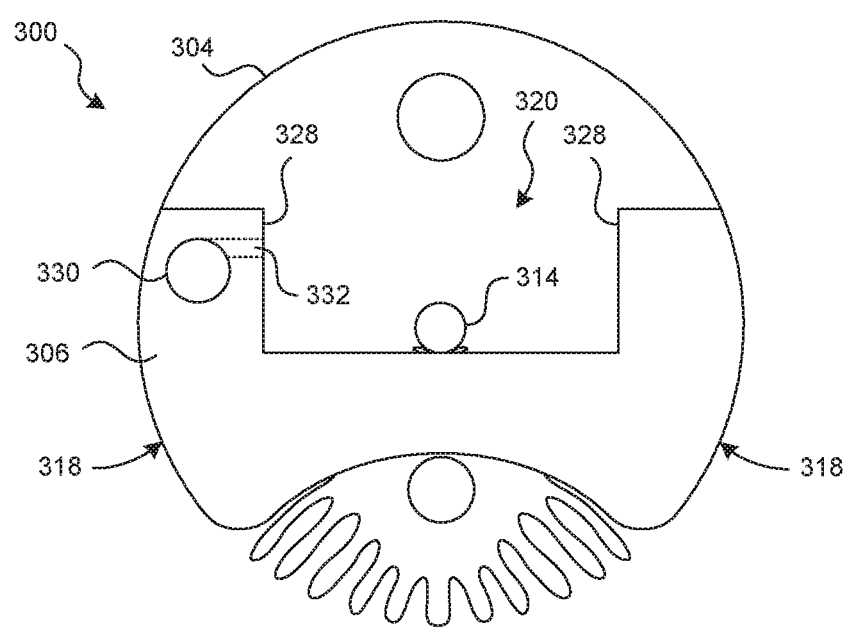
FIG. 3 is a cross-sectional end view of another embodiment of a second portion of a delivery catheter configured in accordance with the present technology.

FIG. 3 is a cross-sectional end view of another embodiment of a second portion 306 configured in accordance with the present technology. The second portion 306 of FIG. 3 can be generally similar to the second portion 106 of FIGS. 1A-1C, except the second portion 306 of FIG. 3 includes one or more flushing lumens 330. The flushing lumen 330 can extend distally from a fluid source (not source) positioned at the proximal portion of the delivery catheter through a sidewall 318 to an exit port 332 positioned at an interior surface 328 of the corresponding sidewall 318. As such, the flushing lumen 330 can infuse one or more fluids (such as saline) into the cavity 320 during a procedure to improve echolucence and thus visualization during the procedure.

II. Visualization Devices

FIG. 4A is a side view of one embodiment of a visualization device 400 for use with the any of the delivery catheters 100, 200 or 300 described above. As shown in FIG. 4A, the visualization device 400 can be an intravascular ultrasound ("IVUS") device that includes an elongated shaft 406 configured to be slidably received by the visualization lumen of the delivery catheter (not shown), and one or more transducers 402 and receivers 404 positioned along the shaft 406. The transducers 402 are configured to emit ultrasound signals S, and the receivers 404 are configured to receive the emitted signals after the emitted signals are reflected by adjacent biological matter (e.g., tissue, blood, etc.). Although only one transducer 402 and one receiver 404 are shown in FIG. 4A, the visualization device 400 can include more than one transducer 402 (e.g., two, three, four, etc.) and/or more than one receiver 404 (e.g., two, three, four, etc.). Additionally, the transducer and receiver can be a single element, such as a piezoelectric element. In some embodiments, the visualization device 400 can include a lumen 408 that extends distally from a proximal, extracorporeally-positioned portion of the visualization device 400 to an exit port 410. The lumen 408 can be configured to slidably receive a guidewire and/or fluid therethrough.

FIG. 4B is a cross-sectional end view of the visualization device 400 shown in FIG. 4A taken along line 4B-4B. Referring to FIGS. 4A and 4B together, the transducer 402 can be configured to emit ultrasound signals in a fan-shape plane parallel to the longitudinal axis of the delivery catheter (not shown). The emitted ultrasound signals (S) can span an angular width a (FIG. 4A) of between about 45 degrees and about 180 degrees. In some embodiments, the emitted ultrasound signals (S) can span an angular width a of between about 80 degrees and about 160 degrees. In some embodiments, the emitted ultrasound signals (S) can span an angular width α of between about 100 degrees and about 145 degrees.

FIG. 5A is a side view of a visualization device 500 configured in accordance with another embodiment of the present technology. FIG. 5B is a cross-sectional end view of the visualization device 500 shown in FIG. 5A taken along line 5B-5B. The visualization device 500 of FIGS. 5A and 5B can be generally similar to the visualization device 400 of FIGS. 4A-4B, except the visualization device 500 of FIG. 5A includes an additional transducer and receiver (labeled 502b, 504b, respectively) positioned circumferentially opposite to the first transducer and receiver 502a, 502b about the shaft 506. As such, the visualization device 500 is configured to emit (and receive) ultrasound signals in opposite radial directions simultaneously to compile a more complete image of the local anatomy.

Figure 6A:
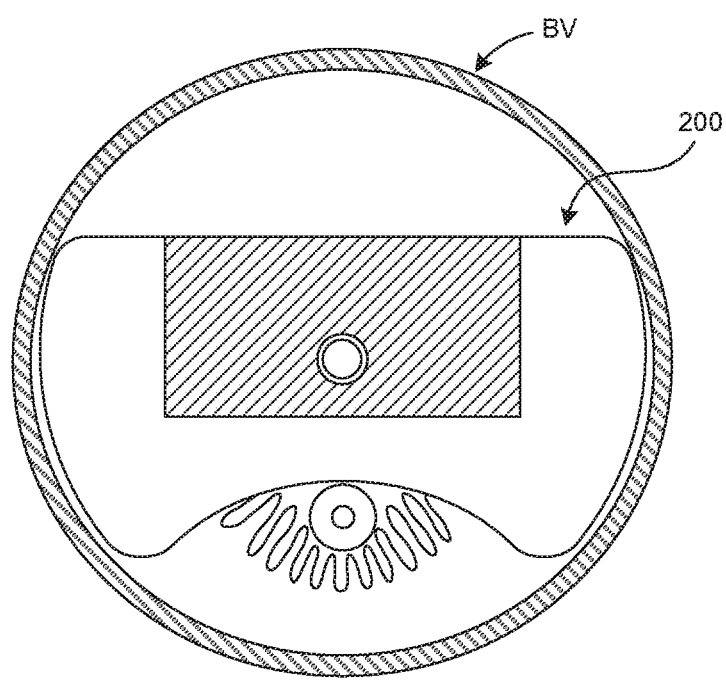
FIGS. 6A-6C illustrate one example for creating an autologous valve with a delivery catheter configured in accordance with the present technology.
Figure 6B:
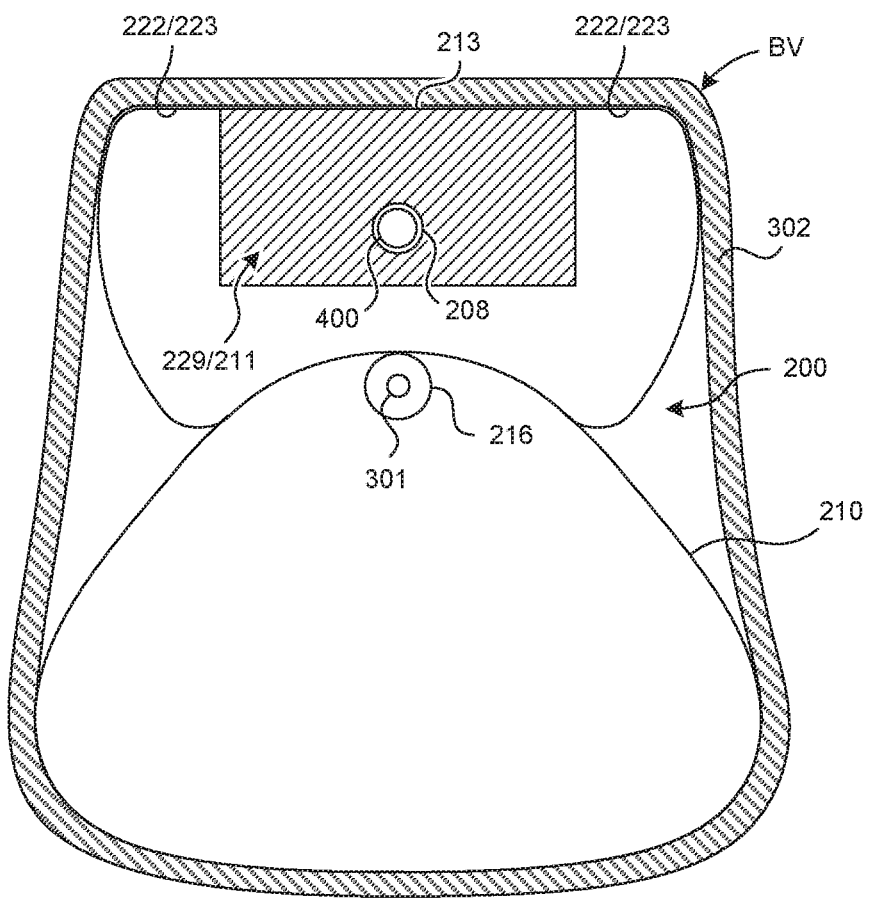
Figure 6C:
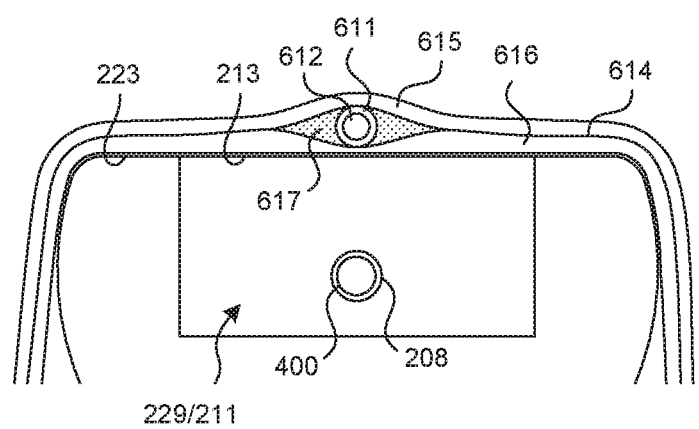

III. Selected Methods for Utilizing the Delivery Catheter for Creation, Repair, Maintenance and/or Removal of Valves For purposes of explanation of the devices, systems and methods of the present technology, FIGS. 6A-6C illustrate one example for creating an autologous valve (e.g., a venous valve) with the delivery catheter 200 shown in FIG. 2. It will be appreciated that the process described with respect to FIGS. 6A and 6C can instead be implanted with catheters 100 or 300.

To begin, the delivery catheter 200 can be intravascularly delivered to a target location in a blood vessel BV, as shown in FIG. 6A. Next, as shown in FIG. 6B, the expandable element 210 can be expanded or inflated to force the tissue engaging surface 223 against the vessel wall 302 of the blood vessel BV such that the tissue is stretched taut across the tissue engaging surfaces 223 and the superior surface 213. As can be seen, the vessel wall 302 is stretched taut by the inflation of the expandable element 210. The planar orientation of the vessel wall portion across the superior surface 213 and the tissue engaging surfaces 223 places the tissue in a known reference frame relative to the imaging lumen 208 and the device lumen (not shown in FIG. 6B). Additionally, the visualization device 400 or 500 (FIGS. 4A-5B) is shown slidably disposed within the imaging lumen 208, and is surrounded by saline within the imaging lumen.

FIG. 6C is a cross-sectional view showing a puncture element 611 in the process of dissecting the vessel wall V along a dissection line 614 to separate layers 615 and 616 and thereby form a dissection pocket 617. In one embodiment, the puncture element 611 can have a lumen 612 through which a fluid flows under pressure to separate the layers 615 and 616 from each other using hydrodissection. One aspect of the catheter 300 is that by stretching the vessel wall taut against the engaging surfaces 223, it confines the corners of the hydrodissection pocket 617 to the engaging surfaces 223. As such, the lateral extent of the dissection pocket 617 is limited by the engaging surfaces 223. After fully forming the dissection pocket 617, the puncture element 611 is removed and an expansion tool can then be advanced distally from the device lumen exit port (not shown in FIG. 6C) and between the layers 615 and 616 of the vessel wall 611 (e.g., the medial and adventitial layers of the vessel wall).

Figure 7:
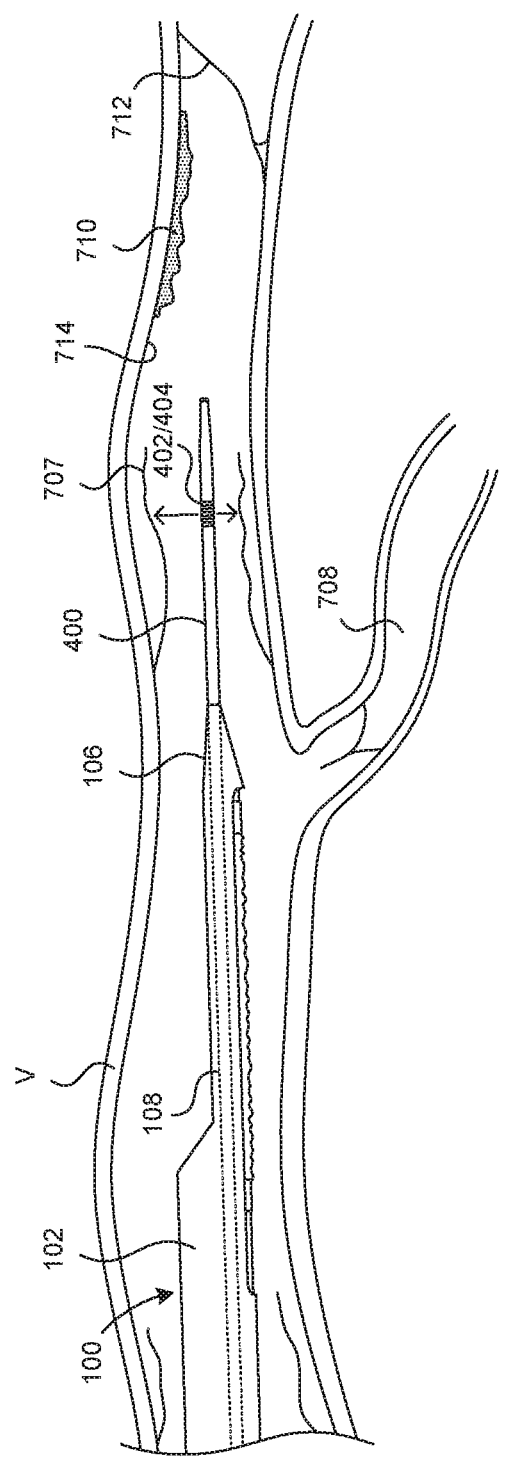
FIG. 7 is a side view of a distal portion of a delivery catheter positioned in a blood vessel in accordance with the present technology.

A. Selected Embodiments of Devices, Systems, and Method for Identifying a Treatment Region FIG. 7 is a side view of the distal portion 100 of the delivery catheter 100 positioned within a blood vessel V. As shown in FIG. 7, a visualization device 400 can be extended distally out of the distal exit port (not shown) and past the distal end of the second portion 106. A diseased blood vessel can contain many structures indicative of malfunctioning that can be imaged circumferentially when the visualization device 400 is in the distal configuration. Such structures can include natural vein valves (NV) 707, collateral vessels (CV) 708, fibrotic wall thickening (F) 710, intraluminal synecchia (S) 712, and others. The distal configuration can be used to evaluate portions of the vessel wall adjacent to the visualization device to locate a "clean section" (CS) 714 of the vessel wall; that is, a portion of the vessel wall that presents an improved surface for leaflet creation (e.g., free from diseased structures). Upon locating such a clean section 714 of vessel wall, the visualization device 400 can be retracted to a position proximal of the visualization lumen exit port (see FIG. 1C).

For some procedures, it may be beneficial for the clinician to utilize the visualization device 400 to aid in the navigation of the delivery catheter 100 through the tortuous blood vessels to a target location. In such embodiments, the visualization device 400 can be advanced distally past the second portion 106 and move through the vessel of interest before inserting the delivery catheter 100 into the body (not shown).

B. Selected Embodiments of Devices, Systems, and Methods for Informing Tissue Apposition Some embodiments of a delivery catheter require use of an expandable element to force a vessel wall to conform around a specific geometry provided by the geometry of a catheter surface. Because different vessels have different luminal diameters and shapes, and because different vessel walls have different thicknesses and compliance, a single force or pressure of apposition is not generally used in all vessels. It is useful therefore to have real time feedback as to the degree of apposition at a point in time during the activation of an expandable element.

Figure 8A:
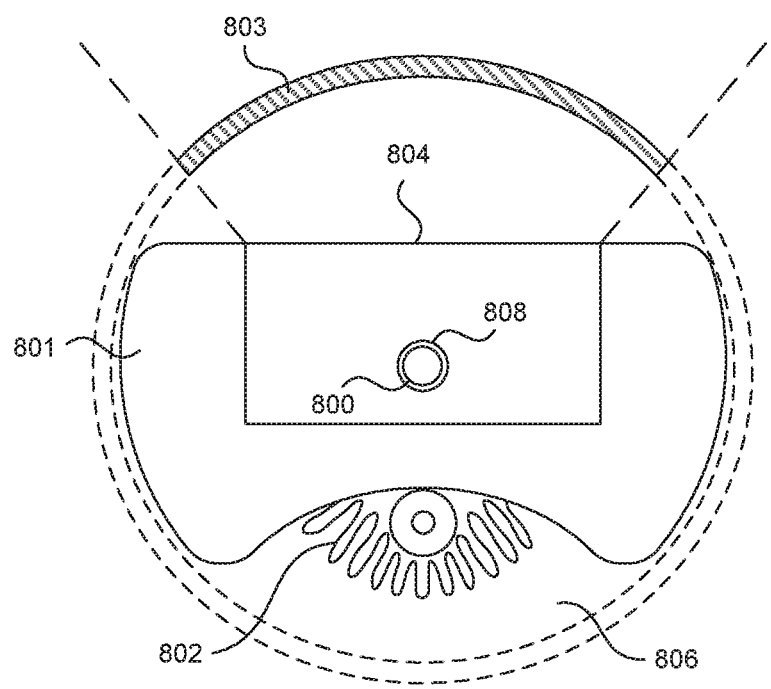
FIGS. 8A-8C are cross-sectional views of the operation of a delivery catheter configured in accordance with the present technology.
Figure 8B:
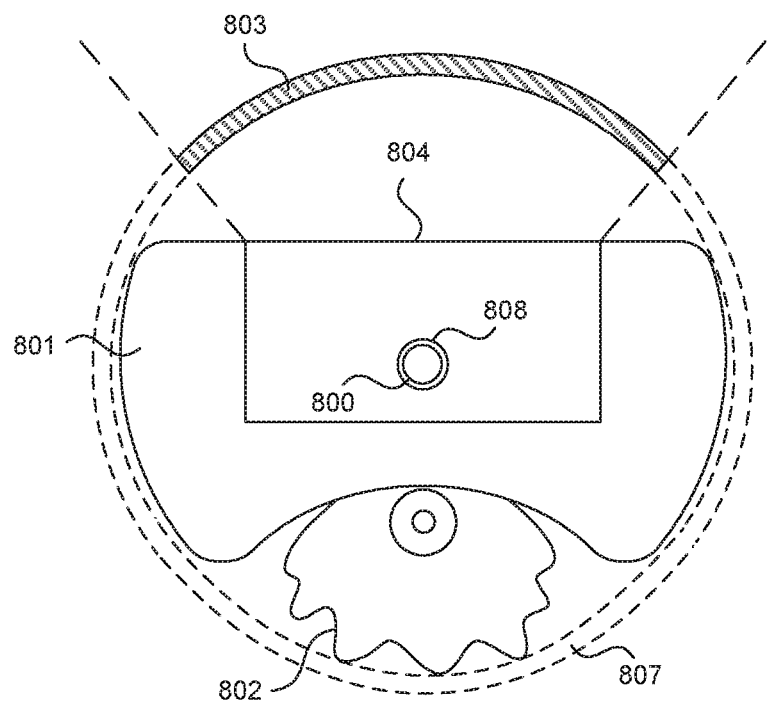
Figure 8C:
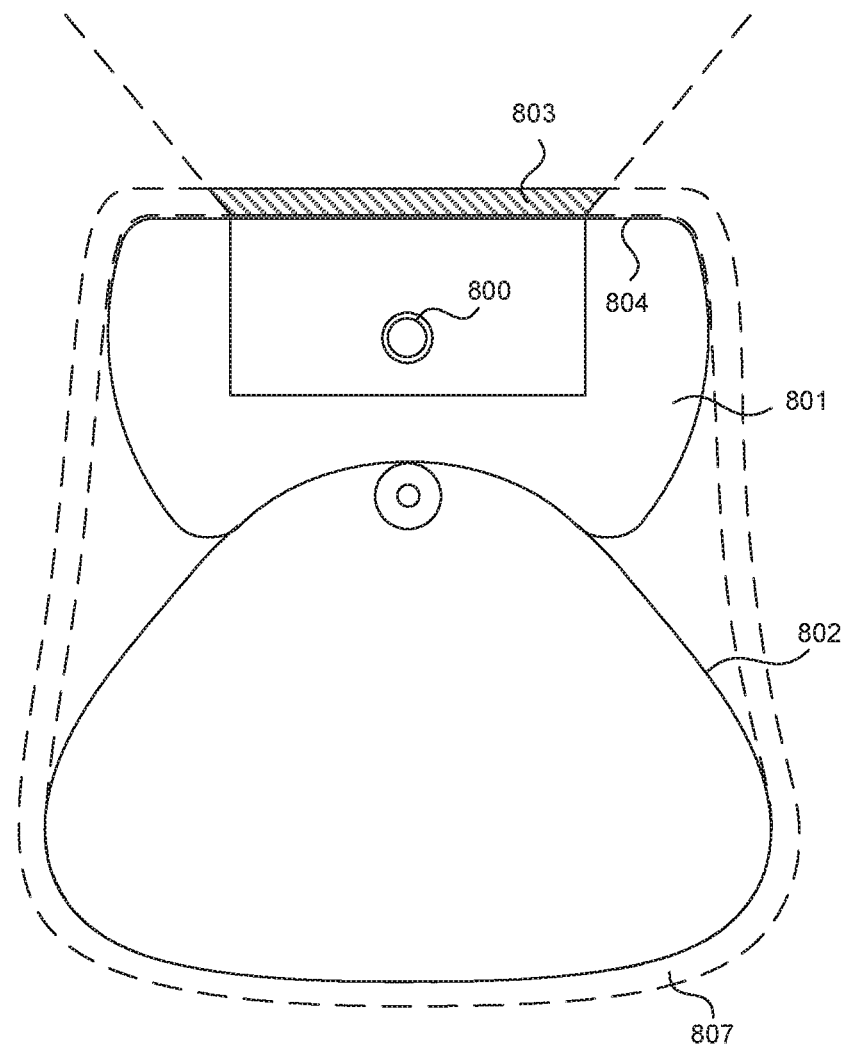

FIG. 8A is a cross-sectional view of a catheter 801 having a compliant balloon 802 that can be inflated to project away from the bottom side of the distal end of the delivery catheter 801. As the balloon 802 expands, it forces the top side of the vein wall 803 against a flat reference surface 804 of the delivery catheter 801. FIG. 8B, for example, shows an intermediate step in which the balloon 802 is partially inflated such that it begins to push on the bottom side of the vein wall 807. The balloon 802 according moves the flat reference surface 804 of the catheter 801 towards the top side of the vein wall 803. Using a visualization device 800 located within a visualization lumen, the clinician can visualize this relative movement between the vein wall 803 and the reference surface 804. This allows the clinician to understand that the balloon 802 must be further inflated to gain proper vein wall apposition. FIG. 8C depicts the point at which the apposition balloon 802 has been inflated enough to force the top side of the vein wall 803 into tight apposition with the reference surface 804 of the catheter 801. Upon seeing this contact, the clinician can stop inflating the balloon 802 to prevent damage to the vessel or the catheter.

Figure 9A:
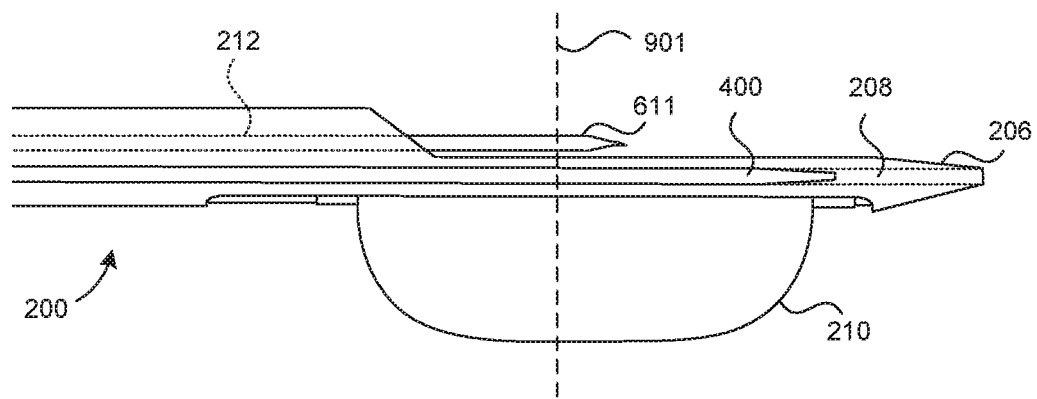
FIG. 9A is a side view and FIG. 9B is a cross-sectional view of the operation of a delivery catheter configured in accordance with the present technology.
Figure 9B:
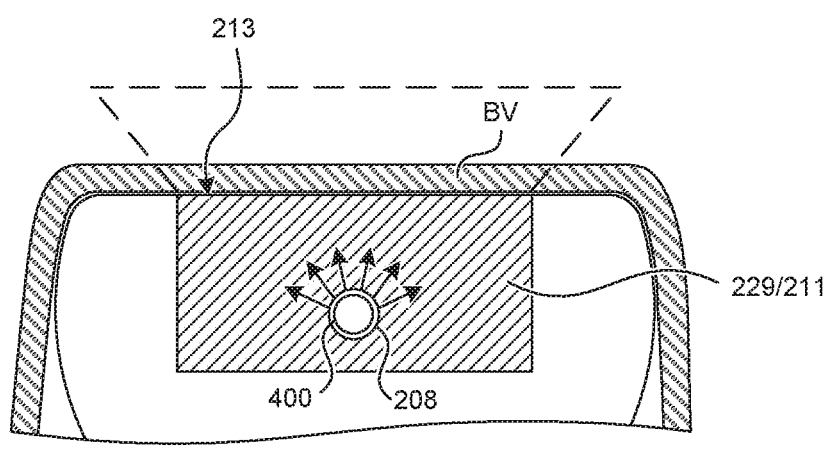

FIG. 9A is a side view of an embodiment of the catheter 200, and FIG. 9B is a cross-sectional end view of a portion of FIG. 9A. It will be appreciated that other catheters, such as catheters 100 and 300, can be used in the process shown in FIGS. 9A and 9B. FIGS. 9A and 9B depict the top half of the catheter 200 during activation of an expandable element 210. Upon retraction of the visualization device 400 to a point where the transducers are proximal to the distal tip of the second portion 206, a clear image of a specific section of vascular wall is imaged as it conforms to the reference surface 213 of the catheter body.

FIG. 9A shows an "apposition assisted imaging" configuration in which the location of the visualization device 404 permits an imaging plane 901 distal to the puncture element exit port at the end of the device lumen 212, but proximal to the distal end of the catheter itself (similar to the distal configuration from FIG. 1). Simultaneously, the expandable element 210 (e.g., balloon) is actuated to force the vessel wall (not pictured) against the reference surface 213 as shown in FIG. 9B. At this point, a puncture element (e.g., puncture element 611 shown in FIG. 6C) can be advanced from the distal exit port of a device lumen (e.g., device lumen 207 shown in FIG. 2) to dissect the vessel wall as described above.

Figure 10A:
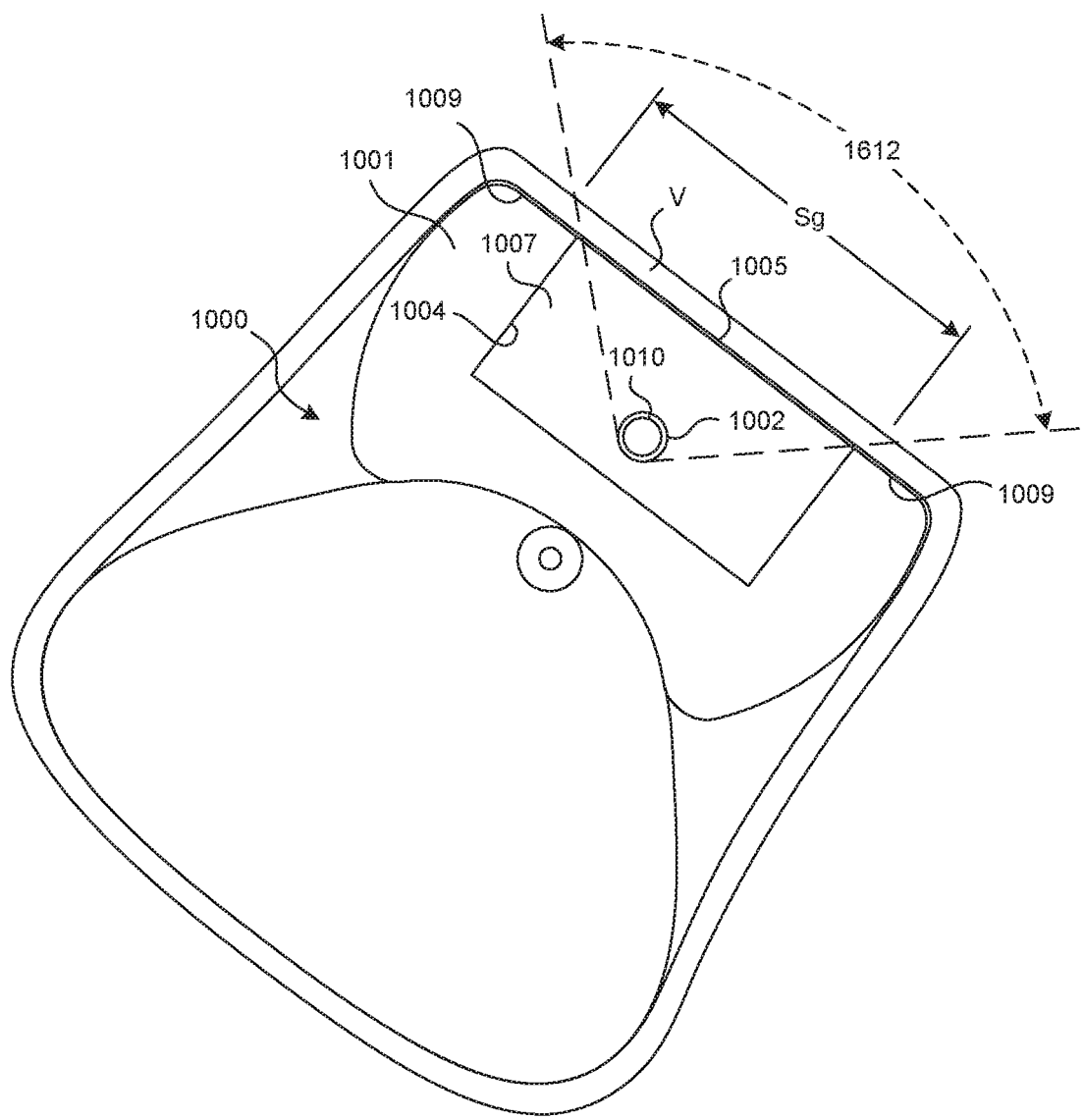
FIGS. 10A and 10D are cross-sectional views.
Figure 10D:
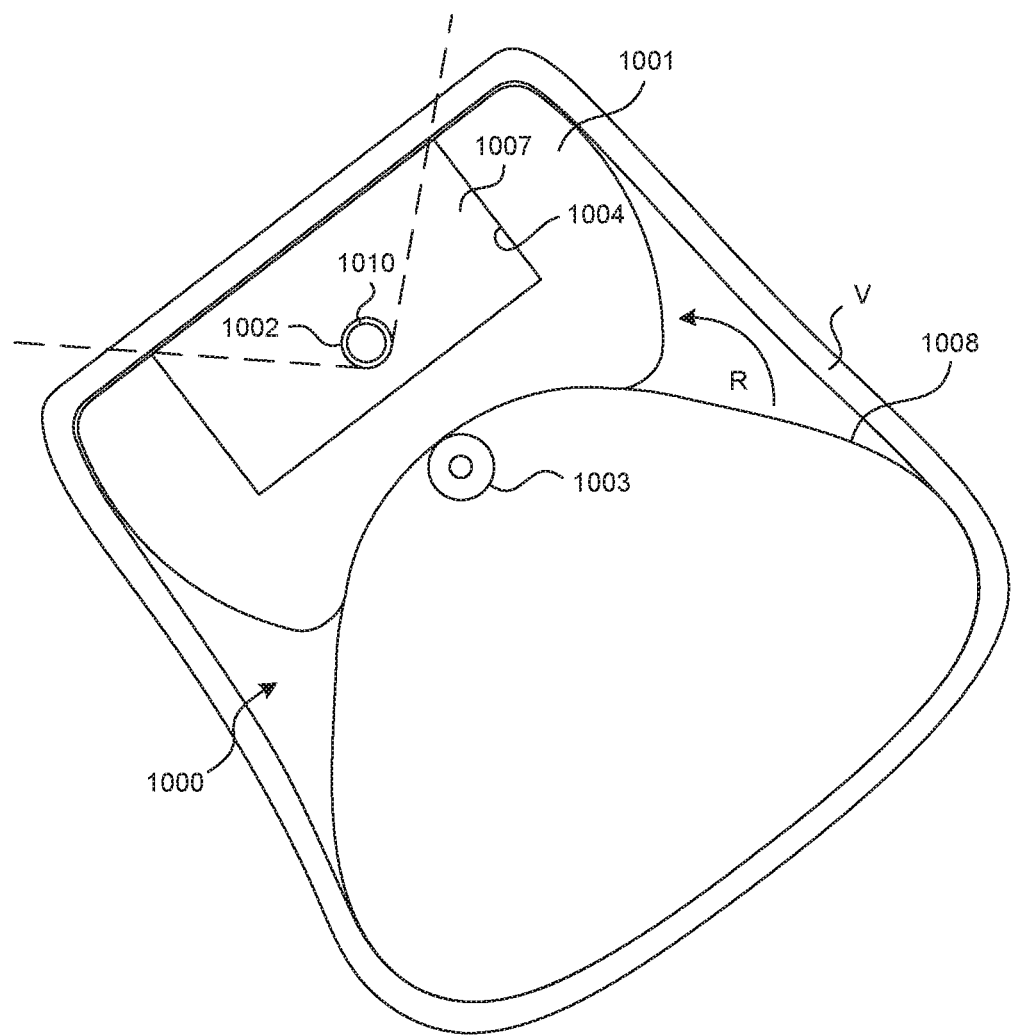

In addition to assessing the extent of wall apposition, several aspects of the present technology are also useful for rendering a three-dimensional (3D) image of a vessel. FIGS. 10A-10D depict an apposition catheter 1000 which can be used to accurately reconstruct a 3D image of a vessel wall due to its ability to shape and locate a vessel wall with respect to an visualization device. The apposition catheter 1000 can be similar to portions of the catheters 100, 200 and/or 300 described above. In the illustrated embodiment, the apposition catheter 1000 includes a body 1001, a visualization lumen 1002, an inflation lumen 1003, a cavity 1004, and an imaging window 1007 defined by the cavity 1004. The opposition catheter 1000 can also include a reference portion 1005 defined, at least in part, by engaging surfaces 1009, and an opposition balloon 1008 or another type of expandable structure (e.g., a Nitinol braid). In operation, a visualization device 1010, is located at the imaging window 1007. The imaging window 1007 may be an open cavity or a material through which visualization can be achieved, as previously described. As shown in FIG. 10A, when the balloon 1008 is inflated, the vessel wall V conforms to the reference portion 1005. As shown in FIG. 10B, the visualization device 1010 has an imaging element 1011 that provides an image at a particular plane of visualization 1012. In the method described, the visualization device 1010 is retracted, potentially at a known constant rate, to sweep the imaging plane 1012 through a volume of vessel wall V. FIG. 10C depicts the visualization device 1010 in the retracted position after it has been swept proximally from the more distal location shown in FIG. 10B. The data from a single retraction (e.g., one pass of the visualization plane 1012 along the longitudinal aspect of the vessel V) produces a 3D image of a longitudinal segment (Sg) of the vessel wall V. To image the entire vessel wall, the entire apposition catheter 1600 can be rotated sequentially (as shown by arrow R in FIG. 10D) and the visualization device 1610 swept longitudinally along each segment until all segments have been imaged. In some embodiments, the balloon 1008 is at least partially deflated to disengage the vessel wall during rotation of the apposition catheter 1000. In other embodiments, the pressure of the apposition balloon is left low enough to allow for rotation of the apposition catheter 1000 without deflation, such that the balloon 1008 and/or the reference portion 1005 can slide along the vessel wall.

In a similar embodiment to that just described, a long plane visualization device can also be used to construct a 3D image of a vessel. In this embodiment, an apposition catheter much like the catheter 1000 can be used in conjunction with the long plane visualization device. The apposition catheter can be rotated, potentially with known and constant speed, to sweep through 360 degrees of the vessel without pulling back of the visualization device at incremental steps.

Figure 11A:
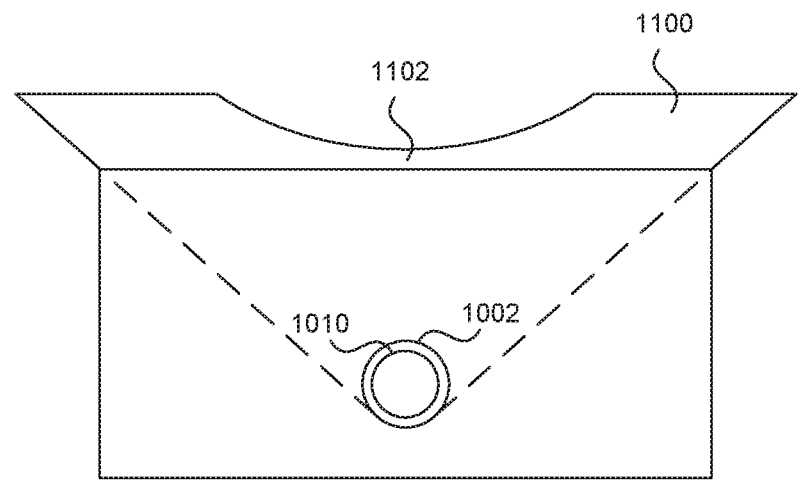
FIGS. 11A and 11B are cross-sectional views of a delivery catheter and a visualization device configured to determine aspects of the tissue of a blood vessel in accordance with the present technology.
Figure 11B:
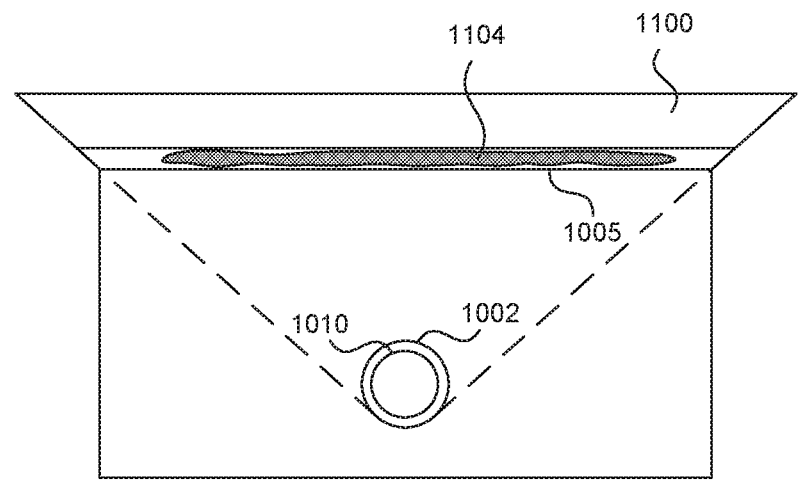

Several embodiments of the present technology are also useful to assess the health and/or procedural suitability of the vessel wall. FIG. 11A depicts the imaging of a vascular wall 1100 with a non-homogenous thickness, due to an extremely thin section 1102. This may direct the clinician to find an alternate location for valve creation. FIG. 11B depicts a native valve leaflet 1104, squeezed between the reference portion 1005 and the vein wall 1100. Additionally, this configuration allows for general evaluation of a vessel wall thickness, layering, cell health, fibrotic composition, vascular composition, rigidity, and other useful characteristics. This composition may also facilitate imaging of structures outside the vessel wall, which may be delicate or vulnerable. This information may be used to direct the valve creation procedure in some way.

C. Selected Embodiments of Devices, Systems and Methods for Informing Vessel Wall Puncture Upon puncturing a vessel wall in a controlled way, it is useful to know the orientation of any given plane. It is also useful to know the location of the puncture element with respect to the vessel wall geometry of the fluid dissection pouch around the puncture element at a given time and in a given plane. Although there are many different potential "states" that could be defined, some important states are: "luminal", "intramural", and "perforated". Knowledge of these states allows particular procedural steps to be confirmed or contingency plans to be initiated as a result of the information.

Figure 12A:
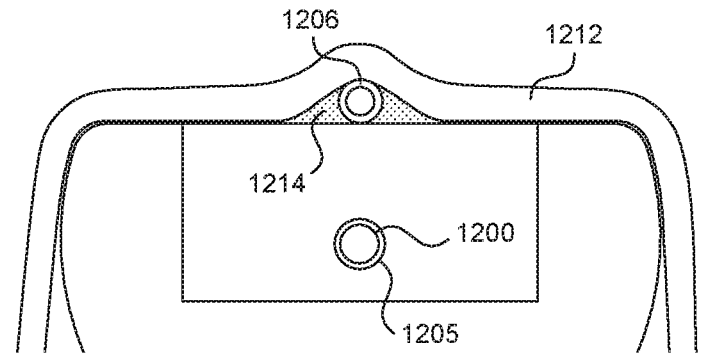
FIGS. 12A and 12B are cross-sectional views illustrating different states of a delivery catheter and visualization device in accordance with the present technology.

FIG. 12A depicts the "luminal" state. As depicted, a needle or puncture element 1206 is flush on top of the flat catheter surface 1208, which can be defined at least in part by echolucent material 140. Also, a visualization device 1200 is slidably disposed within an imaging lumen 1205. In the lumimal state, the puncture element is not within the vessel wall 1212, but rather is in the true lumen of the vessel. At this point, hydrodissection fluid 1214 can potentially be seen surrounding the needle and mixing with blood in the vessel.

Figure 12B:
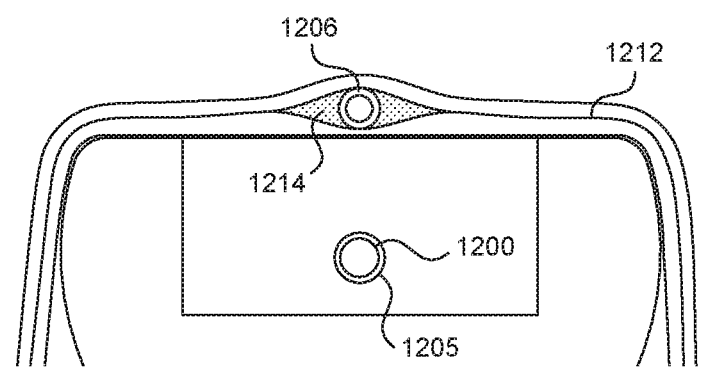

FIG. 12B depicts the "intramural" state. In this state, at least the distal portion of the puncture element 1206 is within the thickness of the vessel wall 1212. As such, the hydrodissection fluid 1214 is initially contained in a pocket in the vessel wall 1212 formed along a true dissection plane without perforation.

Since several embodiments of the technology enable precise visualization to track the depth and location of a puncture element within a vessel wall, it is possible to steer a puncture element in real time. For example, it may be advantageous to direct the puncture element upward toward the adventitial side of the vein wall if the puncture is too low, or conversely direct the puncture element downward if it is too high. One way to accomplish this type of up-down steering is to utilize a beveled needle as the puncture element and rotate the needle to achieve a specific direction of travel. In another embodiment, it might be useful to steer the puncture element left or right depending on whether it has wandered too far to one side or the other. Such left-right movement can be achieved by advancing a shape memory stiffening over-sheath along the puncturing element or other methods for deflecting a long rigid tube.

D. Selected Embodiments of Valve Pockets

FIGS. 13A-13D show how the distal, circumferential imaging modality can be used specifically to determine the depth of a valve pocket (natural or autologously created), the width of a dissection pouch or valve pocket (natural or autologously created), and/or the thickness of valve leaflet (natural or autologously created). FIG. 13A, more specifically, is a side view of the delivery catheter 1300 positioned within the blood vessel BV with the visualization device 400 having a transducer/receiver portion 402/404 longitudinally aligned or adjacent a downstream portion of a leaflet 1320. FIG. 13B depicts an image taken along cross-section 13B-13B in FIG. 13A. Referring to FIG. 13A, the transducer/receiver portion 402/404 is positioned such that an imaging plane 1316 is at the mouth 1318 of a pocket 1324 formed by the valve leaflet 1320. Referring to FIG. 13B, a single image can be used to determine the angular width of the valve mouth using a reference system of the image system (e.g., pixel counts, etc). FIGS. 13C and 13D depict the same two views, but after the visualization device 400 has been advanced distally until it is the near bottom of the valve pocket 1324. By using standard catheter indexing techniques understood by those skilled in the art, this can be used to measure the depth of the pocket. Utilizing processing algorithms, the estimated or exact thickness of the leaflet 1320 can be determined at any point along the length or width of the valve pocket 1324.

Figure 14A:
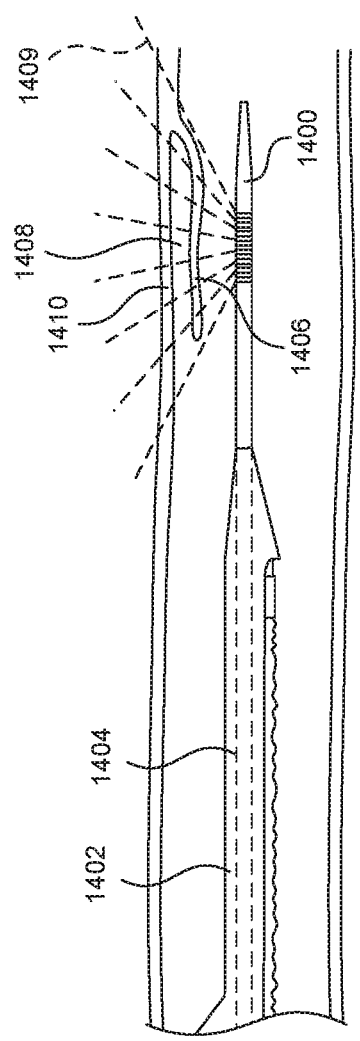
FIG. 14A is a side view of the operation of a visualization device in accordance with the present technology.
Figure 14B:
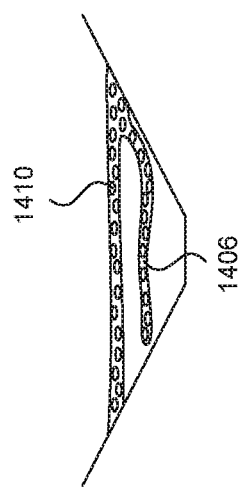
FIG. 14B depicts an image provided by the visualization device of FIG. 14A.

FIG. 14A depicts use of a long plane IVUS visualization device 1400. In this configuration, the long plane IVUS visualization device 1400 is passed through a lumen 1404 of a catheter 1402 until it is positioned beyond the distal end of the catheter 1402. The visualization device 1400 has a long imaging plane along the longitudinal axis such that it can image or view a valve leaflet 1406 and the valve pocket 1408 (natural or autologous) along a single longitudinal imaging plane 1409 positioned at some point along the width of a valve. FIG. 14B shows an image along the imaging plane 1409 from which the clinician can ascertain information about the varying thickness of the leaflet 1406, the depth of the valve pocket, and the thickness of adventitial wall 1410 along the length of the valve. In other embodiments, the long plane IVUS visualization device 1400 can also be used independently with or without a guidewire.

Figure 14C:
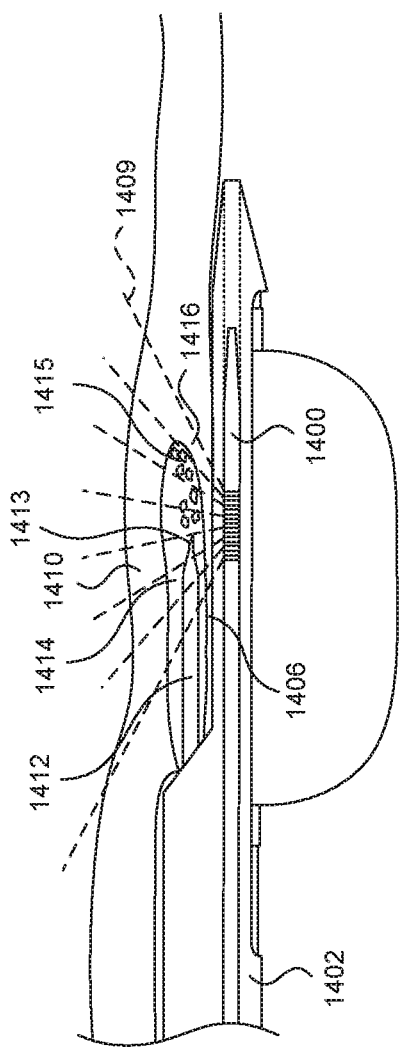
FIG. 14C is a side view of the operation of the visualization device shown in FIG. 14A at a another location in accordance with the present technology.
Figure 14D:
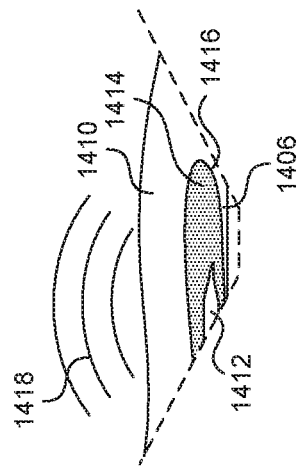
FIG. 14D depicts an image provided by the visualization device at the location shown in FIG. 14C.

FIGS. 14C and 14D depict the use of the long plane IVUS visualization device 1400 in the apposition assisted imaging configuration previously described. In this embodiment, the radial orientation of the visualization device 1400 can be specifically controlled such that the imaging plane 1409 intersects a puncture element 1412 disposed within the catheter 1402. This could be accomplished with catheter configurations similar to or the same as those described in FIGS. 1 and/or 2. As can be seen in FIG. 14C, the imaging plane 1409 is positioned to capture information on both sides of the distal tip 1413 of the puncture element 1412. As can be seen in the depiction of the IVUS image of FIG. 14D, such a configuration allows for the capture of a distal section of the puncture element 1412, as well as a hydrodissection pouch 1414 filled with a hydrodissection fluid 1415, and the bottom of a dissection pouch 1416.

Additionally, the long plane IVUS visualization device and other imaging configurations described can be utilized with an articulating puncture element. In these embodiments, information gained in real time from different imaging modalities may direct the clinician to articulate the puncture element up or down (toward the adventitia or toward the lumen), left or right (counterclockwise about the vessel circumference or clockwise about the vessel circumference), or backward or forward (proximal or distal). Upward and downward movement could be accomplished with rotation of a needle bevel. Left and right could be accomplished with use of a shape memory puncture element. Back and forth can be accomplished with translational actuation on the proximal end.

In several embodiments utilizing IVUS imaging, a fluid that serves as an acoustic contrast agent may also be used for hydrodissection, flushing, or marking a location to assist with visual markers and differentiation of tissue planes. Such agents may include saline with micro air bubbles, fluids with a density significantly higher or lower than blood, or other fluids that otherwise have different acoustical properties than blood or surrounding tissues.

Figure 15:
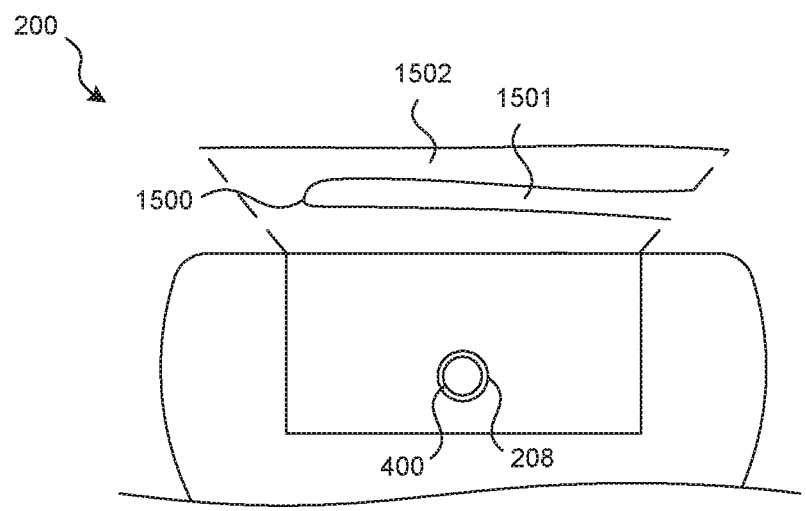
FIG. 15 is a cross-sectional view of a delivery catheter and a visualization device determining and aspect of a dissection pocket in accordance with the present technology.

FIG. 15 is a cross-sectional view showing how the corner or border 1500 of a dissection pouch 1501 within a vascular wall 1502 can be determined. For example, the visualization device 400 can be positioned using the catheter 200 along the dissection pouch 1501 to measure the width of valve pocket 1501 or valve mouth. This can be done by determining the radial location of one corner 800 of a dissection pouch, then disengaging the expandable element, rotating the catheter to a desired position and then re-engaging the expandable element until the other corner of the dissection pouch is found. This method can be used to measure the angular width of a dissection pouch, or autologous valve leaflet, or natural valve leaflet, etc.

E. Assist in Identifying Fixation Devices

Figure 16A:
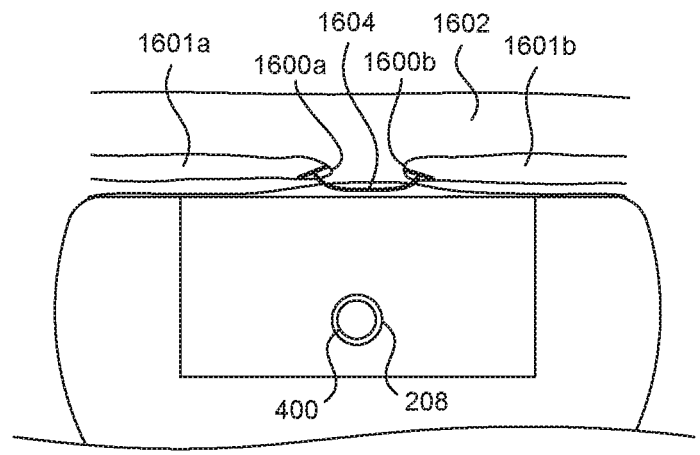
FIGS. 16A-16D are cross-sectional views of a catheter and visualization device used to implant clips, sutures or other types of devices in accordance with the present technology.

FIGS. 16A-16D illustrate aspects regarding how apposition assisted imaging can also be utilized to identify a specific feature within a vein wall. This type of visualization can be used to assess or facilitate fixation (i.e. clipping, suturing, tissue welding, gluing, or otherwise joining) of autologous or natural valve leaflets to each other or to a vascular wall. FIG. 16A is a cross-sectional view of the catheter 200 and visualization device 400 being used to confirm that a double sided T-tag clip 1604 that has been successfully placed between commissures 1600a,b of two separate valve pockets 1601a,b. Utilizing the visualization configuration with the visualization device 400 may also allow for real time tensioning of this type of T-tag clip.

Figure 16B:
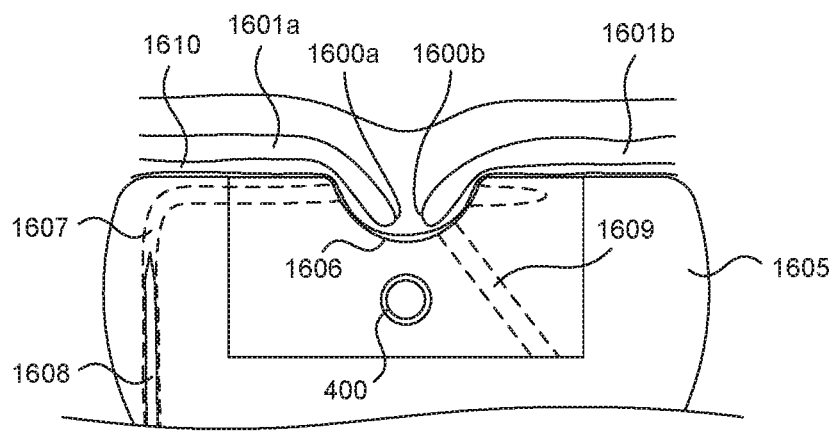
Figure 16C:
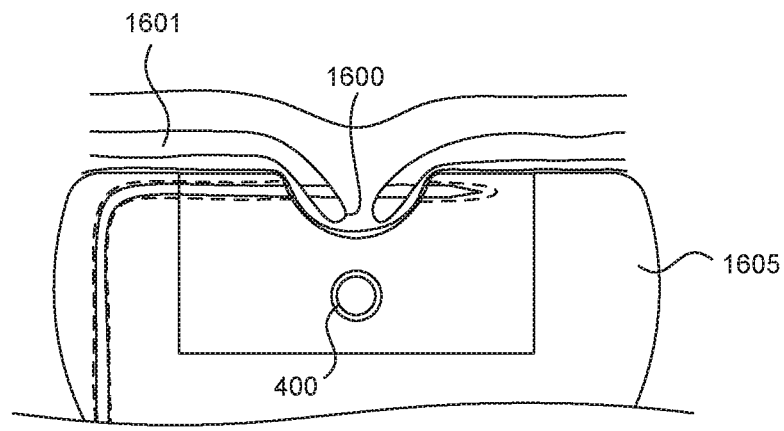
Figure 16D:
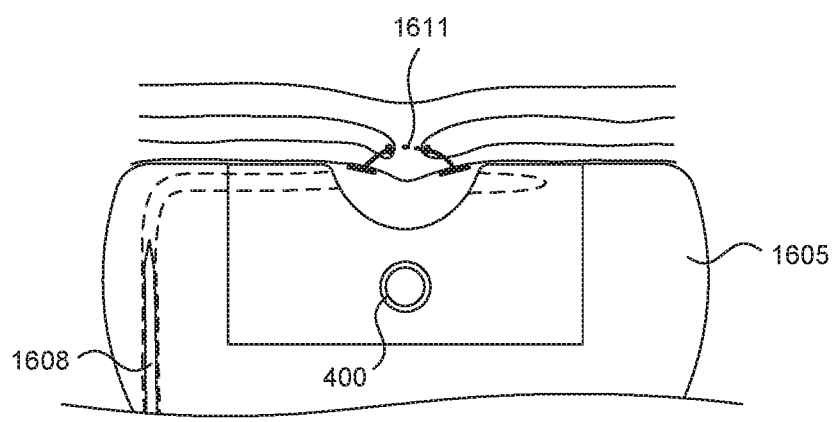

The foregoing visualization configurations can also be used to assist in placing a fixation element such as that described. For example, FIG. 16B shows a main apposition catheter 1605 with an apposition surface 1610 having a curved recess 1606 configured to accept tissue upon apposition. The catheter 1605 can also have a suction lumen 1609 configured to provide a suction force through a port into the recess 1606 to further assist with drawing vein wall tissue into the recess 1606. With this configuration, the visualization device 400 can be used to visualize where two autologous or natural commissures 1600a,b are with respect to the recess 1606. The main apposition catheter 1605 can be rotated with visual assistance (with or without deactivation of the expandable element, not pictured) until the commissures 1600a,b align with the recess 1606 as shown in FIG. 16B. At this point, a suction is drawn through the suction channel 1609 to draw the tissue in. The catheter 1605 also has a puncture lumen 1607 that enters (and potentially exits) the recess. As depicted in FIG. 16B, a needle 1608 is disposed to slide within the puncture lumen 1607. Referring to FIG. 16C, the needle can pass laterally through the recess 1606 and puncture the vessel wall such that the needle 1608 passes through both valve pockets 1601a,b and commissures 1600a,b. The needle 1608 can exit the luminal side of the vessel wall and then extend back into a continuation of the puncture lumen 1607 on the opposite side of the recess 1606. In selected embodiments, the needle 1608 can be used to deploy a double sided T-Tag 1611, suture, or another type of clip that can winch the two commissures closer together. Once the needle is retracted out, a pusher rod (not pictured) can force the T-Tag to remain within the vessel wall and expand into a predefined shape to provide the necessary tension between the commissures. The T-Tag may be made from Nitinol, Stainless Steel, silicone, or another shape memory plastic of some kind, and it can be joined with a narrow string of stainless steel or suture like material, that may or may not be tensionable under real time visual feedback.

IV. Other Embodiments of Delivery Systems and/or Visualization Devices and Accompanying Devices and Methods A. Linked Devices FIGS. 17A and 17C are side views of a linked actuation mechanism that moves of the visualization device (and therefore the advancement of the visualization plane) with a tool of interest. In one embodiment a visualization device 1700 is translationally linked in a proximal location 1702 to a puncture element 1704 (here a needle). FIG. 17A depicts this configuration when the puncture element 1704 has just emerged from an exit port 1706 and punctured into a vascular wall 1701. FIG. 17B depicts an IVUS image from the imaging plane 1708 shown in FIG. 17A. Note the imaging plane 1708 is slightly distal to the puncture element 1704. In this particular embodiment, this relative location is chosen so that the imaging plane samples a hydrodissection pouch 1710 that is created by the puncture element 1704, but does not image the puncture element 1704 itself. This may be advantageous because if the puncture element 1704 is made from a metallic material, it may distort the image if it is within the imaging plane 1708. Also, this may be advantageous as it gives information about the space where the puncture element 1704 is about to enter as it is advanced distally. FIG. 17C depicts the same configuration after the puncture element 1704 and the visualization device 1700 have been advanced forward to a more distal location. FIG. 17D depicts an image at the location of the imaging device shown in FIG. 17C. The proximal linkage 1702 maintains the relative distance between the distal end of the puncture element 1704 and the imaging plane 1708 in FIGS. 17A and 17C. The proximal linkage 1702 may be temporary (clinician actuated and disengageable) or permanent (bonded or mechanically connected in manufacturing).

The relative position between the puncture element 1704 and the visualization device 1700 can be selected to provide difference benefits. For example, the proximal linkage 1702 may be set such that the imaging plane 1708 matches up near exactly with the distal end of the puncture element 1704. In an alternate embodiment, the proximal linkage 1702 may be set such that the imaging plane 1708 is some small distance proximal to the distal end of the puncture element 1704. In some embodiments, use of a contrast agent may be used as the hydrodissection fluid, to make the hydrodissection pouch 1710 more visible on an ultrasonic image. Also, as described above, a long-plane visualization device can also be mated proximally with the puncture element to synchronize advancement. In this configuration, radial linking is also useful to insure imaging plane intersects with the puncture element.

B. Devices, Systems and Methods for Accommodating Optical Coherence Tomography

Figure 18A:
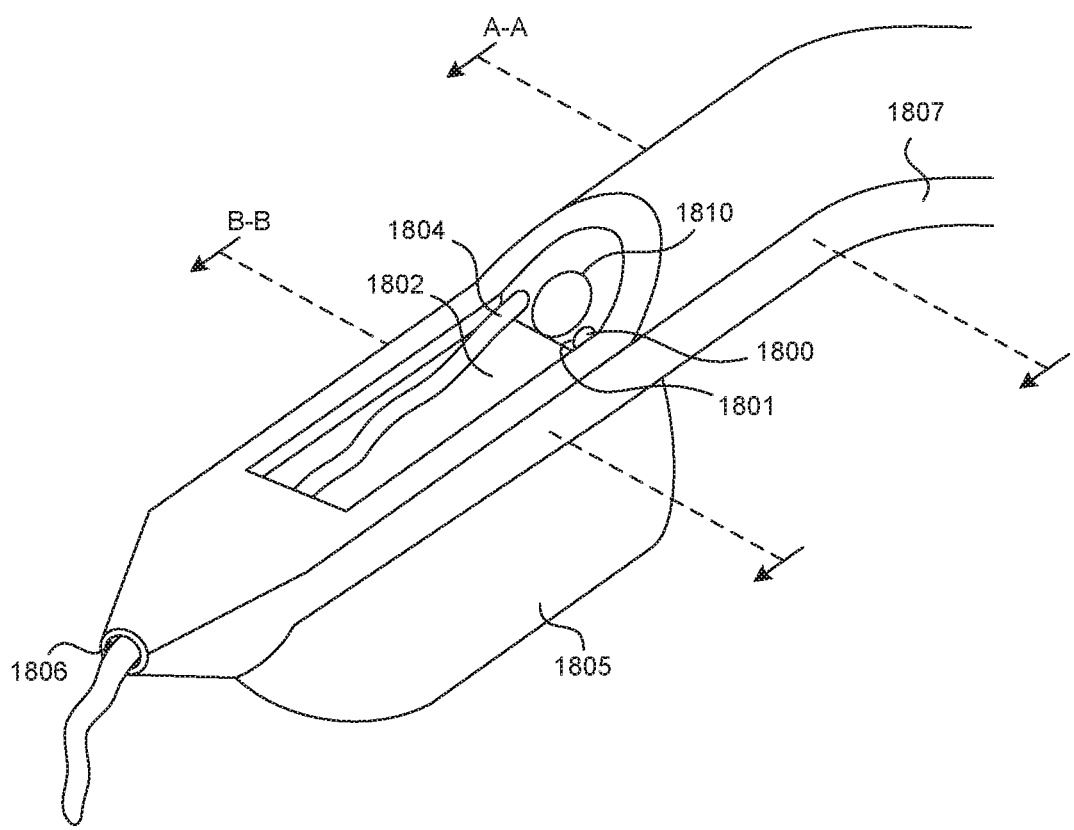
FIG. 18A is an isometric view and FIGS. 18B and 18C are cross-sectional views illustrating a delivery tool and a visualization system in accordance with another embodiment of the present technology.
Figure 18B:
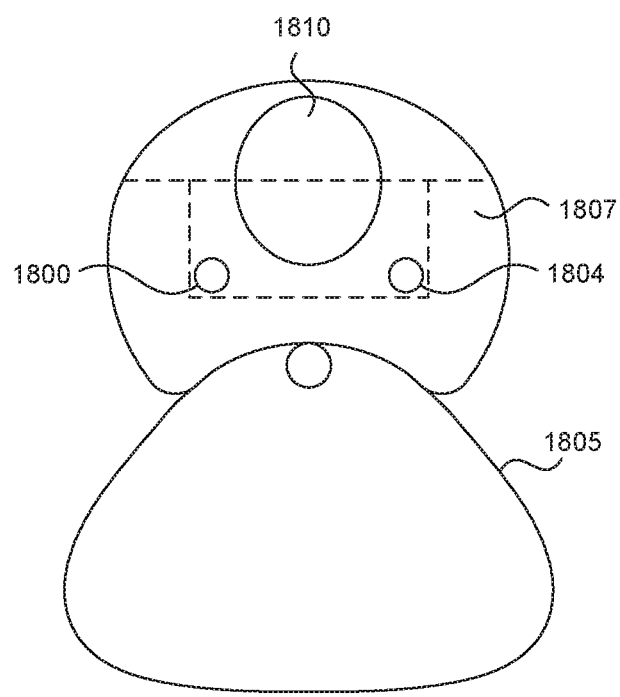
Figure 18C:
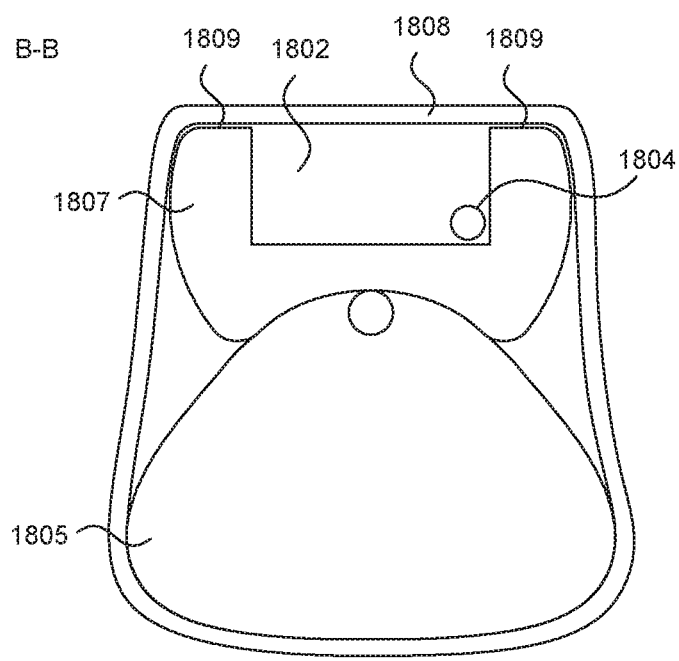

As previously mentioned, OCT can be used in place of the IVUS in the previously described embodiments. In OCT applications, the catheter can have a flush lumen 1800 and exit port 1801 within the visualization area 1802. FIG. 18A shows an embodiment in which the visualization area 1802 is a recessed trough which can house an OCT catheter 1804. Referring to FIGS. 18B and 18C, upon apposition of the vein wall by inflation of an apposition balloon 1805 (FIG. 18B), the visualization area 1802 is sealed from new blood and can be flushed with saline through the flush lumen 1800 (FIG. 18C). The blood that was previously in the visualization area 1802 can be evacuated through the distal nose 1806 (FIG. 18A) of the main catheter 1807 (which can also be used to advance the OCT catheter distal 1804 of the main catheter 1807). Referring to FIG. 18C, the OCT catheter can properly image the vein wall 1808 as it contacts the catheter rails 1809 because the blood is flushed from the visualization through 1802 and the vein wall 1808 is a fixed distance from the OCT catheter 1804. The main catheter 1807 can also have a tool port 1810 for other actions such as vessel wall dissection, manipulation, or valve creation.

Other embodiments utilizing OCT imaging in this context can utilize the configuration described, except with the imaging lumen being positioned parallel to, but in very close proximity to the flat surface of the catheter. In this example, an echolucent material can be replaced by a translucent material such as clear silicone, glass, clear plastic, or saline. Similarly, an embodiment using IVUS may utilize a configuration without any material between the imaging lumen/sheath and the plane created by the flat surface of the rails. Again, with OCT as an imaging modality, it may be advantageous to position the imaging lumen parallel to, but in very close proximity to the flat surface of the rails 1809. For example, it may be advantageous to set this distance to be between 0.001 mm and 3 mm. In other embodiments, it may be advantageous to set this distance to be between 0.01 mm and 2 mm. In other embodiments, it may be advantageous to set this distance to be between 0.25 mm and 0.5 mm.

In other embodiments used in conjunction with OCT imaging, the fluid used to create the hydrodissection pocket may be also act as contrast for light based imaging. For example, an iodine based contrast may be used. In other embodiments, simple saline may be sufficient to obtain proper contrast between tissue and the hydrodissection fluid.

C. Selected Embodiments of Automated Advancement

Figure 19:
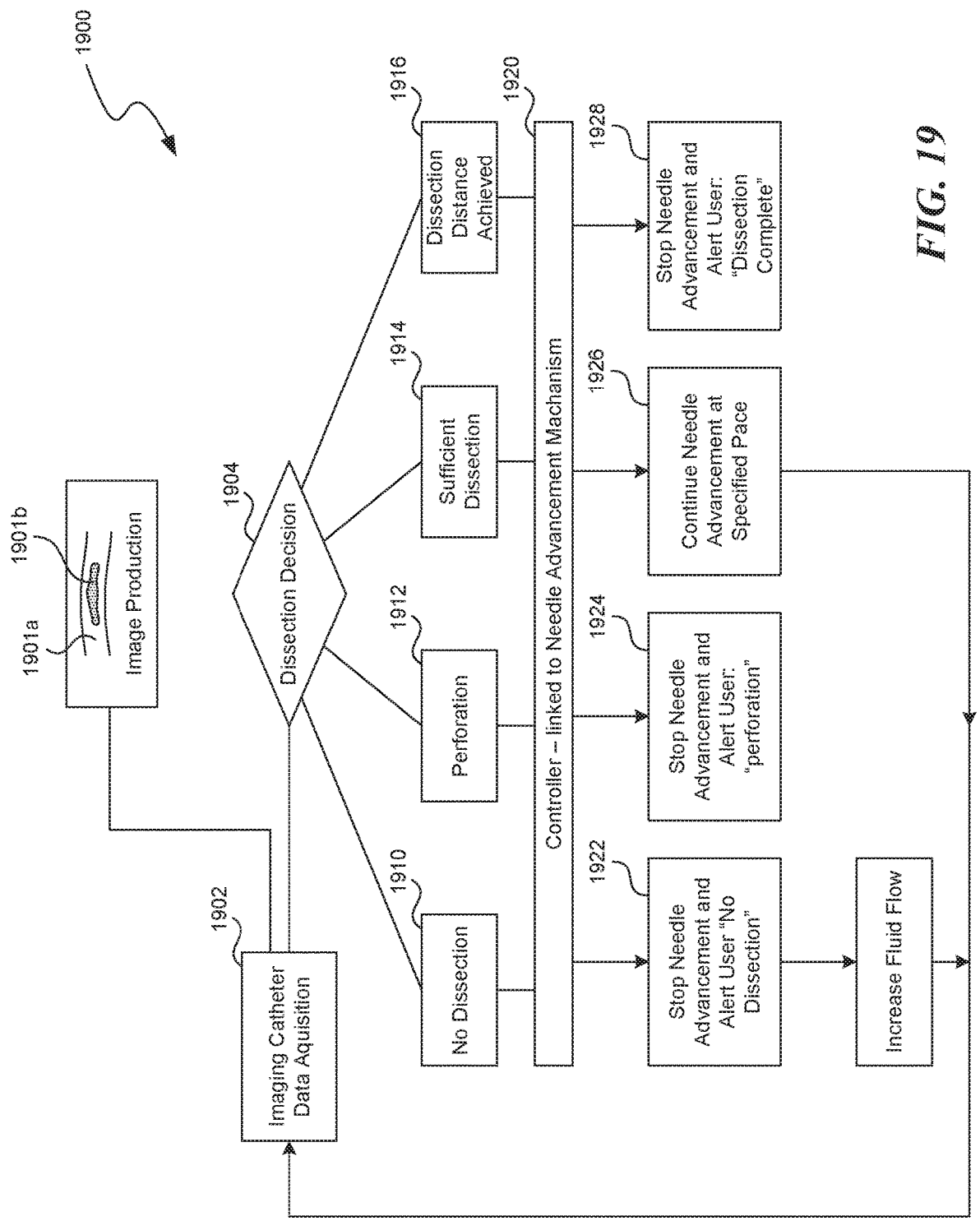
FIG. 19 is a flowchart of an automation algorithm for performing a tissue dissection in accordance with the present technology.

In another embodiment, a visualization method (as described) can be utilized to automate the advancement of a puncture element. An automation algorithm 1900 depicted in FIG. 19 can be utilized with any of the foregoing catheter configurations in conjunction with an IVUS visualization device, OCT visualization device, or a direct visualization device. In the embodiment depicted, the imaging plane acquired is some small distance ahead of a puncture element or needle that is being advanced within a vessel wall. In this embodiment, a mechanism for automated advancement of a puncture element can include a servo-motor or other type of linear motion machine linked to a controller. The controller can advance the needle at a desired pace or stop the needle depending on the status. The controller can also increase or decrease the flow of fluid being injected through the puncture element. FIG. 19 depicts how an image can be acquired from an visualization device that produces an image for the clinician. The data to be analyzed by the algorithm involves the image pertaining to the vein wall 1901a and the size, the change in size with time, the position, and/or the change in position with time of the fluid filled pouch 1901b. This data is interpreted based on these and potentially other variables to make an automated decision about the safety and efficacy of continued advancement of a puncture element. If the dissection detection algorithm does not detect a dissection in the vein wall 1901a, the controller will stop the needle advancement, and alert the clinician. As depicted, it may also try other mechanisms to reinitiate a pocket, such as increasing fluid flow through the needle. In similar algorithm embodiments, the controller may back the needle up, or rotate the needle, and then continue again with the same steps.

In one embodiment, the dissection control algorithm 1900 includes acquiring image data from the imaging catheter (block 1902). The algorithm proceeds with a dissection decision (block 1904) that determines whether there is no dissection (block 1910), perforation (block 1912), sufficient dissection (block 1914), and/or dissection distance has been achieved (block 1916). If no dissection is detected (block 1910), the controller stops needle advancement and sends a "No Dissection" alert (block 1922). If the dissection detection algorithm detects a perforation (block 1912), the controller will stop moving needle and alert the clinician (block 1924). If the dissection detection algorithm detects that the dissection is sufficient for continued dissection (block 1914), the controller continues to advance the needle at the desired pace (block 1928). If the dissection detection algorithm detects that the dissection pouch has been created with sufficient length (block 1916), the controller will stop the moving needle, control the fluid flow, and alert the clinician (block 1928). Other automation algorithms can be used depending on the clinical situation. The same basic automated puncture element advancement algorithm can be used with other imaging planes, such as those even with the tip of the needle/dissector.

D. Methods And Devices for Creating Visual Landmarks with Imaging Systems

Figure 20A:
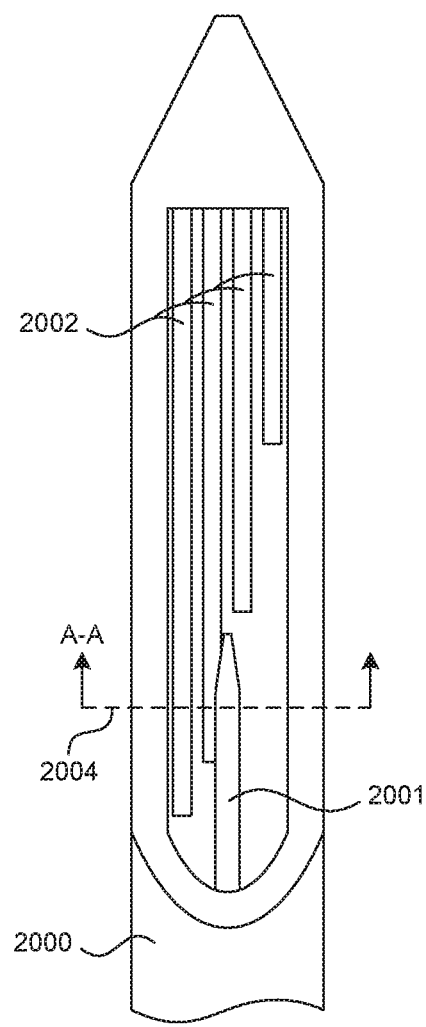
FIG. 20A is a plan view and FIG. 20B is a cross-sectional view of a catheter having structures for indicating the longitudinal location of an imaging plane along the catheter in accordance with the present technology.
Figure 20B:
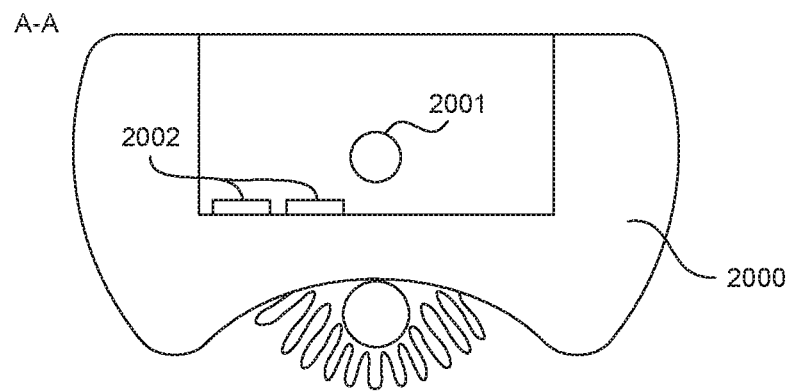

In embodiments involving imaging modalities, it is often useful to provide visual landmarks for determining the position of the imaging plane relative to the delivery catheter. FIGS. 20A and 20B show a main catheter 2000 with structure that can be used to identify the location of the visual plane. FIG. 20A is a top view of the main support catheter 2000 and a visualization device 2001 that images along an imaging plane 2004 as shown. The catheter 2000 can have markers 2002, such as small rectangular protrusions along the bottom surface of the visual field. FIG. 20B depicts a cross section of the catheter along the imaging plane 2004. As can be seen, at a given longitudinal position along the main support catheter 2000, only two of the rectangular markers 2002 can be seen in the imaging plane 2004. As such, a clinician will know that the imaging plane 2004 is between the ends of the second and third markers. In this way, as the visualization device 2001 is advanced or retracted, the clinician can get an approximation for the location of the imaging plane within a given range between the ends of the markers 2002.

In some embodiments, the addition of new markers can be spaced at known distances, such as every centimeter, or every millimeter or every inch. In other embodiments, the markers may simply be added or subtracted at certain critically important places along the catheter (i.e. at the distance at which the pocket depth of a vessel wall dissection is sufficient). In other alternate embodiments, the rectangular protrusions can be replaced by protrusions of other shapes such as half circles or triangles. Additionally, the protruding markers can be replaced by indentations of any shape. In other similar embodiments, a physical material that has a characteristic signature in a certain visualization modality can be used within another material, or bonded to another material within the main structural catheter described.

E. Methods and Devices for One-Way Visualization Schemes

Figure 21A:
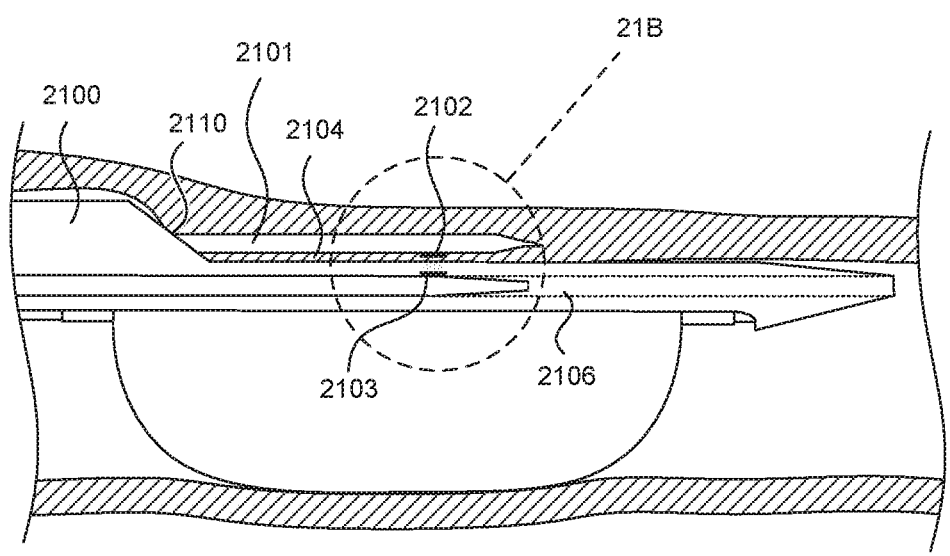
FIG. 21A is a side view of a system for providing an image of tissue in accordance with the present technology.
Figure 21B:
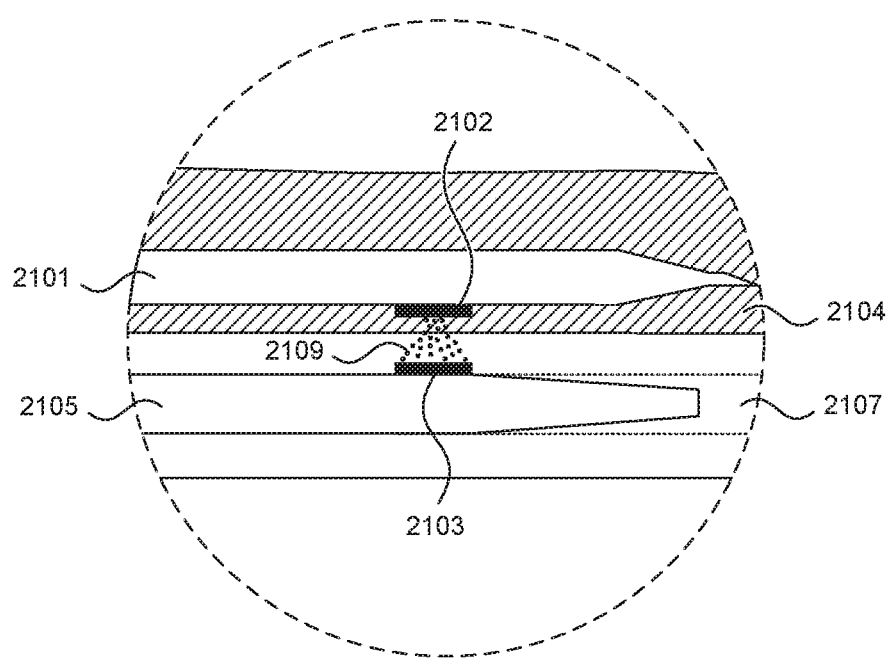
FIG. 21B is a detailed view of a portion of FIG. 21A.

The apposition catheter with visualization configuration described herein, can also be used with a one way visualization scheme that may provide higher resolution information in different dimensions of interest. FIG. 21A shows an apposition catheter 2011 that engages a vessel wall 2104 by expansion of an expandable element 2108 as described herein. The catheter 2100 can include a visualization lumen 2107 configured to receive a signal receptor catheter 2105, and the signal receptor 2105 can have an image receptor 2103 at one or more locations. The apposition catheter 2100 also has a puncture element lumen 2110 through which a puncture element 2101 can be advanced into a vessel wall 2109 or other type of tissue. In the illustrated embodiment, the puncture element 2101 has a signal emitter 2102 near its distal end. FIG. 21B is a detailed view showing the emitter 2102 in the process of emitting energy 2109, such as acoustic energy, light, or electromagnetic energy. In some embodiments, the energy 2109 is functionally one-dimensional pulses. In other embodiments, the energy 2109 are two-dimensional, planar waves. The energy 2109 is emitted downward, through the vessel wall tissue 2104 (or the tissue that the particular puncture element is within), through the vessel lumen, through the apposition catheter 2100, through the visualization lumen 2017, and onto the image receptor 2103. A signal is then routed to a device external to the body where the signal is processed into an image. Due to the fixed distance between the emitter 2102 and the receptor 2103, a very precise gain can be applied to produce a high-resolution image of the tissue 2104 between the emitter 2102 and the receptor 2103. This may be useful in determining (a) if the puncture element is in fact within a vessel wall 2104 or (b) the thickness of the vessel wall at the dissection.

In other embodiments, the image emitter 2102 may be located on the visualization device 2105, and the energy 2109 may be directed upward toward the puncture element 2101 on which a signal receptor 2103 is located. In some embodiments this is a one-dimensional pulse that simply gives the thickness of tissue between the emitter and receptor. In other embodiments this is a two-dimensional planar wave that images cellular composition of the tissue between the emitter and receptor

V. EXAMPLES

The following examples are illustrative of several embodiments of the present technology:

1. A method, comprising:
   intravascularly delivering a delivery catheter to a target location adjacent a vessel wall;
   engaging the vessel wall along a portion of the delivery catheter;
   determining the location of a first circumferential periphery of a dissection pouch formed within the vessel wall;
   determining the location of a second circumferential periphery of the dissection pouch; and
   determining an angular width of the dissection pouch based on the location of the first circumferential periphery and the second circumferential periphery.

2. The method of example 1 wherein determining the location of the first circumferential periphery includes imaging at least one of the first circumferential periphery and the second circumferential periphery with a visualization device of the delivery catheter.

3. The method of any of examples 1 and 2 wherein determining the location of the first and second circumferential peripheries includes analyzing an image of the first and second circumferential peripheries taken by an intravascular visualization device delivered through the delivery catheter.

4. The method of any of examples 1-3 wherein engaging the vessel wall includes expanding an expandable element of the delivery catheter.

5. The method of any of examples 1-4, further comprising decreasing the cross-sectional area of the expandable element after determining the location of the first circumferential periphery.

6. The method of any of examples 1-5, further comprising rotating at least one of the delivery catheter and a visualization device of the delivery catheter after determining the location the first circumferential periphery.

7. The method of any of examples 1-6, further comprising expanding the expandable element after determining the location of the first circumferential periphery.

8. The method of any of examples 1-7 wherein the angular width is a first angular width, and wherein the method further comprises:
   changing the longitudinal position of at least one of the delivery catheter and a visualization device of the delivery catheter;
   determining a circumferential position of a third circumferential periphery of the dissection pouch, wherein the third circumferential periphery is longitudinally offset from the first and second circumferential peripheries;
   determining a circumferential position of a fourth circumferential periphery of the dissection pouch, wherein the fourth circumferential periphery is longitudinally offset from the first and second circumferential peripheries; and
   determining a second angular width based on the third circumferential periphery and the fourth circumferential periphery, wherein the second angular width is longitudinally offset from the first angular width.

9. The method of any of examples 1-8, further comprising rotating at least one of the delivery catheter or a visualization device of the delivery catheter after determining the third circumferential periphery.

10. A method, comprising:
    intravascularly delivering a delivery catheter to a target location adjacent a vessel wall;
    determining the location of a first longitudinal periphery of a dissection pouch formed within the vessel wall; and
    determining a longitudinal depth of the dissection pouch based on the location of the first longitudinal periphery and a second longitudinal periphery.

11. The method of example 10, wherein the first longitudinal periphery is determined by estimating an initial puncture location, and the second longitudinal periphery is determined by determining the distal periphery of the pouch using an imaging process.

12. The method of example 10, wherein determining the first longitudinal periphery comprises determining the location of the initial puncture using an imaging modality, and the method further comprises determining the location of the second longitudinal periphery of the dissection pouch using the same imaging modality.

13. The method of any of examples 10-12 wherein determining the location of the first longitudinal periphery includes imaging the first longitudinal periphery with a visualization device of the delivery catheter.

14. The method of any of examples 10-12 wherein determining the location of the second longitudinal periphery includes imaging the second longitudinal periphery with a visualization device of the delivery catheter.

15. The method of any of examples 10-14, further comprising changing the longitudinal location of at least one of the delivery catheter and a visualization device of the delivery catheter after determining the location the first longitudinal periphery.

16. A method, comprising:
    delivering a delivery catheter to a target location adjacent a wall of a blood vessel;
    creating a dissection pouch within the wall using a puncture element delivered through the delivery catheter, wherein the dissection pouch includes a first wall portion that has been separated from a second wall portion, and wherein the first wall portion define an inner portion facing an interior portion of the vessel and the second wall portion defines an outer portion;
    imaging the dissection pouch using an visualization element delivered through the delivery catheter; and
    determining a physical parameter of the first wall portion based on the image of the dissection pouch.

17. The method of example 16 wherein the first wall portion defines a leaflet.

18. The method of any of examples 16-17 wherein the physical parameter is the thickness of the first wall portion.

19. The method of any of examples 16-17 wherein the first wall portion defines a leaflet, the physical parameter is the thickness of the leaflet, and the thickness of the leaflet is determined at a plurality of locations along the leaflet.

20. The method of any of examples 16-19 wherein the physical parameter is a perforation.

21. The method of any of examples 17-19 wherein the physical parameter is a perforation of tissue associated with the leaflet.

22. The method of any of examples 16-21 wherein imaging the dissection pouch includes imaging a first portion of the dissection pouch and determining a thickness of the leaflet portion includes determining a first thickness of a first portion of the leaflet, and wherein the method further comprises:
    changing the longitudinal position of at least one of the visualization device and the delivery catheter with respect to vessel wall; and
    imaging a second portion of the dissection pouch; and
    determining a second thickness of a second portion of the leaflet, wherein the second portion is longitudinally offset from the first portion of the leaflet.

23. A method, comprising:
    intravascularly delivering a delivery catheter to a target location adjacent a vessel wall;
    creating a dissection pouch within the vessel wall using the delivery catheter;
    determining the location of a first periphery of the dissection pouch;
    determining the location of a second periphery of the dissection pouch; and
    determining at least one of an angular width and a longitudinal depth of the dissection pouch based on the location of the first periphery and the second periphery.

24. The method of example 23 wherein determining the location of the first periphery and determining the location of the second periphery includes using a visualization device delivered through the delivery catheter to image the vessel wall.

25. The method of any of examples 23-24, further comprising changing at least one of the a circumferential position, a radial position, and a longitudinal position of the visualization device after determining the location of the first periphery.

26. The method of any of examples 23-25, further comprising changing at least one of a circumferential position, a radial position, and a longitudinal position of the delivery catheter after determining the location of the first periphery.

27. The method of any of examples 23-26, further comprising delivering a treatment device through the delivery catheter to change a dimension of the dissection pouch based on the determination of at least one of the angular width and the longitudinal depth.

Although the invention has been described in terms of particular embodiments and applications, one of ordinary skill in the art, in light of this teaching, can generate additional embodiments and modifications without departing from the spirit of or exceeding the scope of the exampled invention. Accordingly, it is to be understood that the drawings and descriptions herein are proffered by way of example to facilitate comprehension of the invention and should not be construed to limit the scope thereof.

We claim:

1. A delivery system, comprising:
    a delivery catheter comprising a proximal portion having an outer surface and a distal portion configured to be delivered to a target location adjacent to a wall of a blood vessel, wherein the distal portion comprises—
        a slanted surface extending from the outer surface and angled toward a central axis of the distal portion;
        a device lumen terminating at a first exit port along the slanted surface;
        a visualization lumen spaced apart from the device lumen;
        a tissue engagement surface extending from the slanted surface in a longitudinal direction parallel to the central axis of the distal portion, wherein the tissue engagement surface is recessed from the outer surface of the proximal portion and defines a plane radially between the device lumen and the visualization lumen, and wherein the tissue engagement surface is spaced radially apart from the visualization lumen by a fixed distance; and
        a trough defined by sidewalls extending away from the tissue engagement surface and spaced apart from each other at the tissue engagement surface such that the trough is open to the blood vessel along a longitudinal segment of the tissue engagement surface; and
    a puncture element configured to extend out of the first exit port of the device lumen to separate the wall of the blood vessel into a first wall portion and a second wall potion,
    wherein the visualization lumen terminates at a second exit port open to the trough and is configured to receive a visualization element extending along a path aligned with the trough.

2. The delivery system of claim 1 wherein, when the visualization element is advanced through the trough, the delivery catheter is configured to allow for imaging of a cross-section of the vessel wall to determine a physical parameter of the first wall portion.

3. The delivery system of claim 1 wherein the distal portion of the delivery catheter comprises a distalmost exit port distal to the trough and radially aligned with the second exit port.

4. The delivery system of claim 1 wherein the fixed distance between the visualization lumen and the tissue engagement surface is between about 0.01 mm and about 3.00 mm.

5. The delivery system of claim 1 wherein the tissue engagement surface is defined by two superior surfaces of the sidewalls of the trough, and wherein the superior surfaces are spaced apart from each other and extend distally in the longitudinal direction from the slanted surface.

6. The delivery system of claim 1 wherein the trough comprises an echolucent material between the sidewalls.

7. The delivery system of claim 1 wherein the visualization element is an intravascular ultrasound (IVUS) catheter.

8. A delivery system, comprising:
    a delivery catheter having a distal portion configured to be delivered to a target location adjacent to a wall of a blood vessel, a device lumen having a first exit port, and a visualization lumen spaced radially apart from the device lumen by a fixed distance and having a second exit port, wherein the distal portion comprises—
        a first portion having a first cross-sectional area;
        a second portion extending distally in a longitudinal direction from the first portion, the second portion having a second cross-sectional area less than the first cross-sectional area;
        a tissue engagement surface extending longitudinally along the second portion parallel to a central axis of the second portion; and
        a trough extending longitudinally along the second portion parallel to the central axis, wherein the trough is open to the blood vessel along a longitudinal segment of the tissue engagement surface,
    wherein at least a portion of the first exit port is spaced radially apart from a plane defined by the tissue engagement surface by a first distance in a first direction and is positioned along a transition between the first portion and the second portion, and
    wherein the visualization lumen is spaced radially apart from the plane defined by the tissue engagement surface by a second distance in a second direction opposite the first direction and terminates at the second exit port open to the trough.

9. The delivery system of claim 8, further comprising:
    a puncture element configured to extend through the device lumen beyond the first exit port; and
    a visualization element configured to extend through the visualization lumen beyond the second exit port,
    wherein the trough is configured to guide the visualization element longitudinally and parallel to the puncture element while spaced apart from the puncture element by the fixed distance.

10. The delivery system of claim 8, further comprising a visualization element configured to extend out of the visualization lumen and into the trough while imaging cross-sections of the wall of the blood vessel.

11. The delivery system of claim 10 wherein the visualization element is an intravascular ultrasound (IVUS) catheter.

12. The delivery system of claim 8 wherein the tissue engagement surface comprises superior surfaces of sidewalls that define the trough.

13. The delivery system of claim 12 wherein the second portion has a distalmost exit port, and wherein the distal exit port is distal to the trough and radially aligned with the visualization lumen.

* * * * *

UNITED STATES PATENT AND TRADEMARK OFFICE
CERTIFICATE OF CORRECTION

PATENT NO. : 11,330,975 B2  
APPLICATION NO. : 16/284883  
DATED : May 17, 2022  
INVENTOR(S) : Fletcher T. Wilson et al.

Page 1 of 1

It is certified that error appears in the above-identified patent and that said Letters Patent is hereby corrected as shown below:

In the Drawings

On sheet 25 of 27, in Figure 19, reference numeral 1920, Line 1, delete "Machanism" and insert -- Mechanism --.

In the Specification

In Column 5, Line 41, delete "elastrography." and insert -- elastography. --.
In Column 6, Line 65, delete "a" and insert -- α --.
In Column 6, Line 67, delete "a" and insert -- α --.
In Column 10, Line 34, delete "lumimal" and insert -- luminal --.
In Column 16, Line 36, delete "receptor" and insert -- receptor. --.
In Column 18, Line 60, delete "the a" and insert -- a --.

Signed and Sealed this  
Twenty-seventh Day of September, 2022

Katherine Kelly Vidal  
*Director of the United States Patent and Trademark Office*